(12) United States Patent
Chaudhuri

(10) Patent No.: US 10,568,819 B2
(45) Date of Patent: Feb. 25, 2020

(54) SKIN ENHANCING COMPOSITIONS AND METHODS

(71) Applicant: Sytheon Limited, Boonton, NJ (US)

(72) Inventor: Ratan K Chaudhuri, Lincoln Park, NJ (US)

(73) Assignee: Sytheon Limited, Boonton, NJ (US)

( * ) Notice: Subject to any disclaimer, the term of this patent is extended or adjusted under 35 U.S.C. 154(b) by 0 days.

(21) Appl. No.: 15/798,804

(22) Filed: Oct. 31, 2017

(65) Prior Publication Data

US 2018/0116927 A1 May 3, 2018

Related U.S. Application Data

(60) Provisional application No. 62/415,493, filed on Oct. 31, 2016.

(51) Int. Cl.
| | |
|---|---|
| *A61K 8/35* | (2006.01) |
| *A61Q 19/00* | (2006.01) |
| *A61Q 17/00* | (2006.01) |
| *A61Q 17/04* | (2006.01) |
| *A61Q 19/08* | (2006.01) |

(52) U.S. Cl.
CPC ............... *A61K 8/35* (2013.01); *A61Q 17/00* (2013.01); *A61Q 17/04* (2013.01); *A61Q 19/001* (2013.01); *A61Q 19/08* (2013.01)

(58) Field of Classification Search
CPC ........ A61K 8/35; A61Q 19/001; A61Q 19/08; A61Q 17/00; A61Q 1/04
See application file for complete search history.

(56) References Cited

U.S. PATENT DOCUMENTS

| | | |
|---|---|---|
| 3,708,540 A | 1/1973 | Yokotani et al. |
| 5,853,705 A | 12/1998 | Nakayama et al. |
| 8,765,101 B2 | 7/2014 | Marion et al. |
| 2012/0141395 A1 | 6/2012 | Chaudhuri |
| 2015/0174033 A1 | 6/2015 | Herrmann et al. |
| 2016/0256368 A1 | 9/2016 | Santhanam et al. |

FOREIGN PATENT DOCUMENTS

| | | |
|---|---|---|
| EP | 0797984 A2 | 1/1997 |
| WO | 20120131072 A1 | 10/2012 |

OTHER PUBLICATIONS

International Search Report and Written Opinion for PCT/US2017/059212, Int'l PCT equivalent to instant application, dated Aug. 1, 2018.

*Primary Examiner* — Johann R Richter
*Assistant Examiner* — Genevieve S Alley
(74) *Attorney, Agent, or Firm* — IP&L Solutions; Edward K. Welch, II

(57) ABSTRACT

The present invention relates to compositions and methods for treating and/or preventing chronic- or UV-induced photodamage in the skin as well as damage to the skin caused by chronological aging and disease. Specifically, select aryl alkanones have been found to induce/produce a number of beneficial effects in the skin and skin processes by elevating the skin's defense against UV-induced damage and reversing skin photo- and/or chronological damage in the extracellular matrix (ECM) and dermal-epidermal junction (DEJ), up-regulating tissue inhibitory metalloproteases, reducing oxidative stress, inhibiting activity of matrix metalloproteases, and protecting DNA.

25 Claims, No Drawings

SKIN ENHANCING COMPOSITIONS AND METHODS

RELATED APPLICATION

The present application claims the benefit of U.S. Provisional Application Ser. No. 62/415,493 filed 31 Oct. 2016 and entitled "Methods and Compositions for Topical Applications Using Aryl Alkanones," the contents of all of which are incorporated herein by reference in their entirety.

FIELD OF THE INVENTION

Compositions and methods are described to improve skin appearance by building and defending its function and integrity through reducing up-stream and scavenging down-stream oxidative pathways as well as through recalibrating the expression of genes, proteins, genetic networks and cellular pathways in mammalian skin. Specifically, select aryl alkanones have been found to induce/produce beneficial effects in skin by elevating the skin's defense against UV- and air pollutant-induced damage and reversing skin photo- and/or chronological damage through up-regulation/stimulation of select genes/proteins, especially those associated with or impacting upon the extracellular matrix (ECM) and the dermal-epidermal junction (DEJ); by up-regulating tissue inhibitory metalloproteases; by reducing oxidative stress and inhibiting activity of matrix metalloproteases; and by protecting DNA.

BACKGROUND OF THE INVENTION

Skin aging is a complex process that involves metabolic and physiologic changes that lead to an increasing susceptibility to disease and ultimately death. Besides chronological aging and its impact on human skin and its physiological processes and functions, a number of environmental factors and exposures also have a marked impact upon skin aging, or at least the appearance and manifestation of those consequences associated with or arising from skin aging. Perhaps no environmental factor or exposure is more detrimental to the skin than the exposure of skin to UV radiation which causes a number of diverse biological effects, including sunburn (inflammation), induction of skin cancer (melanoma), premature skin aging, and alteration in cutaneous immune cells (immunosuppression), all of which lead to damage, including permanent damage, of the skin cells. Unfortunately, skin cell damage due to UV radiation is induced by several mechanisms such as UV-induced immuno-suppression, UV-induced DNA damage and accumulation of DNA damaged products, such that efforts to protect the skin, for example, by application of sunscreen, application of moisturizers, post-sunburn treatments and the like, while effective in some respects, are ineffective in others. Rather, for comprehensive photo-protection, especially against premature skin aging, photo-allergies, immune-suppression and skin cancer, it is believed necessary to reverse or reduce UV-induced biochemical changes in the skin.

However, in order to undertake efforts to reverse or reduce UV-induced biochemical changes in the skin one must first appreciate and understand the various UV-induced changes and damage that must be addressed and how those biochemical changes affect the skin and its physiological processes.

DNA Damage and CPDs

The DNA of young people is regulated to express the right genes at the right time to allow the human system to properly function and to protect the body from disease and attack. However, as the years pass the regulation of the DNA gradually gets disrupted: a factor that manifests itself in aging whereby dysregulated DNA increases the risk of different forms of cancer and other diseases. Specifically, the protection of "youthful" DNA diminished. Obviously, health depends on much more than just the regulation of our DNA; however it is clear that dysregulation of the DNA is a fundamental process which increases the risk of different diseases (R C Slieker et al., Age-related accrual of methylomic variability is linked to fundamental aging mechanisms, Genome Biology, 2016; 17 (1) DOI: 10.1186/s13059-016-10536).

There are many molecules in the skin that absorb ultraviolet (UV) radiation; however, one in particular, cellular DNA, strongly absorbs UV radiation, especially shorter wavelength solar UV radiation. It is a well-known fact that chronic exposure to UV radiation, as well as ionizing radiation, leads to DNA damage. This process underlines photo-aging, a term that broadly encompasses changes in the skin associated with life-long exposure to the sun: wrinkling, skin laxity, erythema and hyperpigmentation, among others. More importantly, from a clinical perspective, the role of DNA damage as a, if not the, key provoking event in mutagenesis and tumor development is well-documented. Indeed, DNA damage induced by ultraviolet radiation (UVR) is considered to play a direct part in the initiation, of skin cancers.

While there are various types of UV radiation induced DNA damage in the skin, the most prominent are the dipyrimidine lesions, most especially the cyclobutane pyrimidine dimers (CPDs) and 6-4 pyrimidine-pyrimidone photoproducts. CPDs play major role in skin cancer mutations relative to that of the 6-4 pyrimidine-pyrimidone photoproducts and oxidative DNA damage. Collectively, the data implicate the CPDs as the DNA lesion most strongly involved in human cancers induced by sunlight [G P Pfeifer and A Besaratinia, UV wavelength-dependent DNA damage and human non-melanoma and melanoma skin cancer, Photochem Photobiol Sci, 11:90-97, 2012]. Formation of CPDs also is a molecular trigger for solar-simulated ultraviolet radiation-induced suppression of memory immunity in humans, The mechanism is still under investigation; however, it has been found that CPDs trigger the loss of dendritic cells and infiltration by macrophages [J M Kuchel et al., Cyclobutane pyrimidine dimer formation is a molecular trigger for solar-simulated ultraviolet radiation-induced suppression of memory immunity in humans Photochem Photobiol Sci, 4(8):577-582, 2005]. All told, the CPDs constitute approximately 80% of the total lesions induced or formed by UV radiation exposure, and are believed to influence a large number of cellular functions such as replication, transcription, and DNA repair.

Recent studies have pointed to UVA as a key inducer of CPDs, but not the 6-4 photoproducts (A Tiwari et al., UVA1 induces cyclobutane pyrimidine dimers but not 6-4 photoproducts in human skin in-vivo, J Invest Dermatol, 132:394-400, 2012); whereas, UVB is found to induced both CPDs and the 6-4 photoproducts. Interestingly, the level of UVA-induced CPDs increased with epidermal depth whereas a decrease of UVA-induced CPDs was observed with UVB, suggesting that UVA may be more carcinogenic than has previously been thought.

Additionally, Brash et al have shown that chemiexcitation of melanin derivatives induces DNA photoproducts long after UV exposure has ended [S Premi, D Brash et al, Chemiexcitation of melanin derivatives induces DNA photoproducts long after UV exposure, Science, 347(6224):842-847, 2015]. These authors have further demonstrated that the presence of melanin, activation of NOS (inducible nitric oxide synthase) and NOX (NADPH oxidase), and the triplet state were required for dark CPDs formation. Hence, while one might believe the damage stops once the UV exposure is stopped, these findings indicate otherwise.

Although many, if not most, of the UV radiation induced lesions are efficiently repaired in the skin, such endogenous repair mechanisms to remove DNA lesions and damaged bases are not 100% efficient. Accordingly, CPDs formation still results in various acute effects (erythema, inflammatory responses), transient effects (suppression of immune function), and chronic effects (mutation induction and skin cancer). Despite efforts to raise awareness and teach preventative measures such as sun avoidance, the application of full-spectrum sunscreens, and the use of antioxidant creams, the incidences of both melanoma and non-melanoma skin cancers continue to increase annually and are estimated to be comparable to the sum of all other cancers combined. Given these statistics, it is clear that current preventative measures against skin cancer are insufficient. In fact, neither sunscreens nor topical antioxidants have been shown to effectively block the effects of UV radiation. Essentially, the antioxidants are of limited efficacy and, it seems, the level of these antioxidants contained in the majority of skin creams is too low to have a major impact on free radical damage. Similarly, sunscreens have limited effect as well. Sunscreens absorb only a portion of UV radiation and many fail to be photostable, oftentimes breaking down or degrading even after just a few minutes of sun exposure [H Gonzalez, N Tarras-Wahlberg, B Stromdahl, A Juzeniene, J Moan, O Larko, A Rosen, A M Wennberg, Photostability of commercial sunscreens upon sun exposure and irradiation by ultraviolet lamps, BMC Dermatology, 7:1 (2007) www.biomedicalcentral.com/1471-5945/7/1]. Furthermore, observational studies have repeatedly found sunscreen use to be associated with higher risk of cutaneous melanoma and basal cell skin cancer. This correlation is hypothesized to exist because sunscreens delay the appearance of sunburn, encouraging prolonged sun exposure and thereby increasing skin cancer risk [Yasmeen Kabir, Rachel Seidel, Braden McKnight, Ronald Moy, DNA Repair Enzymes: An Important Role in Skin Cancer Prevention and Reversal of Photodamage—A Review of the Literature, *J Drugs Dermatol.* 14(3):297-301, 2015].

Nitric Oxide (NO) and iNOS Activation

Nitric oxide (NO) plays a pivotal role in human physiology and pathophysiology (Oplender and Suschek, The Role of Photolabile Dermal Nitric Oxide Derivates in Ultraviolet Radiation (UVR)-Induced Cell Death, Int J Mol 14(1):191-204, 2013). It is the smallest known bioactive product of mammalian cells, is highly diffusible and reactive, and can be produced by most cell types. In the human body, NO is formed endogenously by three NO synthase enzymes. The keratinocytes express the neuronal isoform of NO synthase (nNOS), whereas the fibroblasts and other cell types in the skin express the endothelial isoform (eNOS). The third NO synthase enzyme, the inducible isoform of NO synthase (iNOS), is not expressed usually in the skin; but, under certain conditions, virtually all skin cells are capable of expressing iNOS. For example, irradiation of the skin by UVB and/or UVA radiation induces the release of inflammation transmitters, like IL-1, IL-10, TGF-$\beta$1, and TNF-$\alpha$ which induce iNOS to produce higher NO-concentration. iNOS can also be induced by UVB, in the absence of proinflammatory cytokines (Suschek et al., Ultraviolet A1 radiation induces nitric oxide synthase-2 expression in human skin endothelial cells in the absence of proinflammatory cytokines, J Invest Dermatol, 117:1200-1205, 2001). In following, recent studies have confirmed the role of nitric oxide (NO) as a contributor to the UV erythema response [Rhodes L E, Belgi G, Parslew R, et al. Ultraviolet-B-induced erythema is mediated by nitric oxide and prostaglandin E2 in combination. J Invest Dermatol, 117(4):880-885, 2001]. Large amounts of nitric oxide (NO) production following induction of the inducible NO synthase (iNOS) gene has also been implicated in the pathogenesis of various inflammatory diseases. Accordingly, it is generally accepted that high levels of NO are often correlated with inflammatory skin conditions as well as erythema, edema and stimulation of melanogenesis.

It has also been established that NO produced in the skin by NO synthase can combine with superoxide to form peroxynitrile, a highly reactive oxidant and mediator of tissue injury which is found to impair lipid peroxidation itself and oxidize lipid soluble antioxidants (Hogg and Kalyanaraman, Nitric oxide and lipid peroxidation, Biochim Biophys Acta, 1411:378-384, 1999). Indeed, these peroxynitrite radicals are found to react directly with several critical cellular targets including thiols, proteins, lipids and DNA (Current Pharmaceutical Design, 17(35):3905-3932, 2011). The rates of peroxynitrite production in-vivo in specific compartments have been estimated to be as high, as 50-100 $\mu$M per minute. In light of the multiple target molecule reactions, the steady-state concentrations for the peroxynitrite are estimated to be in the nanomolar concentration range and can be sustained for long periods of time. Hence, under certain conditions, exposure to peroxynitrite can be significant owing to both the level and duration of exposure. Furthermore, despite the relatively short half-life of peroxynitrite at physiological pH (~10 ms), its ability to cross cell membranes implies that peroxynitrite generated from a cellular source could influence surrounding target cells within one or two cells diameters. Considering that biological systems exposed to peroxynitrite experience or manifest a multitude of biological effects, including adverse effects on cell viability and function, the degree of potential damage is exacerbated (Szabo et al., Peroxynitrite; biochemistry, pathophysiology and development of therapeutics, Nature Reviews, 6:662-680, 2007).

Reactive Oxygen Species (ROS)

Though there are a number of mechanisms of UV damage in the skin, none is more significant than that due to the action of reactive oxygen species (ROS), also known as free radicals. ROS are generated in increasing quantities with age and are known to damage DNA in general, most especially mitochondrial DNA, as well as cells and tissues. While there is still much to learn, some of the molecular mechanisms upstream of ROS formation have been identified recently with photosensitization by endogenous skin chromophores having emerged as a mechanism linking initial photon absorption with ROS formation in skin (G T Wondarak et al, Identification of Quenchers of Photoexcited States as Novel Agents for Skin Photoprotection, Pharmacol and Experimental Therapeutics, 312(2):482-491, 2005; & references cited therein). Many skin chromophores, including urocanic acid, riboflavin, $B_6$ vitamins, melanin precursors, and porphyrins, are suspected endogenous photosensitizers. Extracellular matrix proteins such as collagen and elastin, which are present in large amounts in the skin and are rich in advanced glycation end products (AGEs) and other cross-link fluorophores, have been identified as potent UVA sensitizers of phot oxidative stress (G T Wondrak et al., Photosensitization of DNA damage by glycated proteins. Photochem Photobiol Sci 1:355-363, 2002). After initial photon absorption, excited singlet states can either relax to the ground state with or without light emission (fluorescence) or undergo intersystem crossing (ISC) with formation of highly reactive biradical triplet states. Photoexcited states exert skin photodamage by direct reaction with substrate molecules, including DNA bases (type I photosensitization) and molecular oxygen (type II photosensitization), leading to ROS formation. Singlet oxygen ($^1O_2$), an electronically excited, highly reactive form of molecular oxygen, is formed after energy transfer between the triplet photoexcited state of the sensitizer and ground state triplet oxygen. $^1O_2$ is a widely accepted example of an excited state mediator of skin photodamage involved in UVA-induced mutagenesis, stress signaling, apoptosis, and remodeling of extracellular matrix components during skin photoaging and carcinogenesis (L O Klotz, K O Kroncke, and H Sies, Singlet oxygen-induced signaling effects in mammalian cells, Photochem Photobiol Sci 2: 88-94, 2003).

Paradoxically, some sunscreens act as potent triplet state UV sensitizers, enhancing light-driven formation of ROS and skin cell photodamage (M Gulston and J Knowland, Illumination of human keratinocytes in the presence of the sunscreen ingredient padimate-O and through an SPF-15 sunscreen reduces direct photodamage to DNA but increases strand breaks, Mutat Res 444: 49-60, 1999). Although moderate skin photo-protection has been demonstrated in many experiments on animal and human skin through topical application of antioxidants (L Packer L and G Valacchi G, Antioxidants and the response of skin to oxidative stress: vitamin E as a key indicator. Skin Pharmacol Appl Skin Physiol 15: 282-290, 2002), the therapeutic effectiveness of skin administration of antioxidants is limited by their sacrificial depletion, their pronounced spontaneous redox chemistry, and their negative interference with the highly regulated skin antioxidant network (A Meves A, S N Stock, A Beyerle, M R Pittelkow, and D Peus, Vitamin C derivative ascorbyl palmitate promotes ultraviolet-B-induced lipid peroxidation and cytotoxicity in keratinocytes. J Investig Dermatol 119: 1103-1108, 2002). Harmful interaction of chemical antioxidants with essential redox signaling in human skin may be anticipated because recent reports point to a significant potential for antioxidant enhanced carcinogenesis in transgenic mice with up-regulated antioxidant responses (Y P Lu, Y R Lou, P Yen, H L Newmark, O I Mirochnitchenko, M Inouye, and M T Huang, Enhanced skin carcinogenesis in transgenic mice with high expression of glutathione peroxidase or both glutathione peroxidase and superoxide dismutase. Cancer Res 57: 1468-1474, 1997).

In light of the foregoing, the role of photoexcited states in skin photodamage and carcinogenesis suggests that direct molecular antagonism of photooxidative stress by physical Quencher of Photo-excited States (QPES) compounds has the potential to reduce skin photocarcinogenesis and photoaging. According to the accepted importance of UVA irradiation in sensitized skin photodamage, QPES are predicted to be most efficacious against photodamage caused by UVA irradiation and are therefore intended for combinatorial use with existing agents for skin photoprotection, especially antioxidants and UV sunscreen actives. Thus, QPES could be a functionally synergistic additive in existing sunscreen formulas and may provide other beneficial effects such as enhancement of photostability of sunscreens (E Chatelain and B Gabard, Photostabilization of butyl methoxydibenzoylmethane (Avobenzone) and ethylhexyl methoxycinnamate by bis-ethylhexyloxyphenol methoxyphenyl triazine (Tinsorb S), a new UV broadband filter, Photochem Photobiol 74: 401-406, 2001).

Mitochondrial DNA

The mitochondrion is a tiny structure inside a cell and is the primary generator of energy, in the form of adenosine tri-phosphate (ATP). Mitochondria have their own DNA which determines all of their functions. Mitochondrial DNA (mtDNA) is made up of 16569 base pairs that, when completely intact, make energy for the body; however, subtle changes in the mtDNA, especially that arising from oxidative damage, have dramatic adverse effects on mitochondrial function and energy production as well as longevity. In following, the mitochondrial clock theory of aging is based upon the progressive accumulation of this oxidative damage, especially that damage arising from reactive oxygen species (ROS).

Over the past decade, researchers have identified and measured various forms of endogenous and environmental mitochondrial DNA (mtDNA) damage and have elucidated mtDNA repair pathways. Interestingly, mitochondria do not appear to possess the full range of DNA repair mechanisms that operate in the nucleus: although mtDNA contains the same types of damage that are targets of each nuclear DNA repair pathway, The reduced repair capacity may, in part, explain the high mutation frequency of the mitochondrial chromosome [S D Cline, Mitochondrial DNA Damage and its Consequences for Mitochondrial Gene Expression, Biochim Biophys Acta, 1819(9-10): 979-991, 2012].

More recently, research around the world has identified a specific deletion (or elimination) in mitochondrial DNA that is known to occur in response to aging and UV exposure [S D Cline, Mitochondrial DNA Damage and its Consequences for Mitochondrial Gene Expression, Biochim Biophys Acta, 1819(9-10): 979-991, 2012; references cited therein]. This deletion is called the common aging deletion or the 4977 base pair deletion; though, it is to be appreciated that there are many other mtDNA deletions that occur in response to aging, such as the 520 base pair deletion, etc. Indeed, it has been found that even minor amounts of this deletion severely alter energy production and cellular function.

Clearly mtDNA is susceptible to endogenous and environmental damage and, unlike other DNA in the human body, lacks the full cohort of nuclear DNA repair mechanisms. Consequently, persistent mtDNA damage poses a threat to mitochondrial gene expression, especially mitochondrial polymerase, whose disruption is believed to underlie much, if not most, skin damage and, consequently, many human diseases.

UV Exposure and Formation of Superoxide via NADPH Oxidase

Nicotinamide adenine dinucleotide phosphate oxidase (NADPH) represents the first step that controls the oxidative stress cascade. Strong evidence suggests that NADPH Oxidase or NOX enzymes are major contributors to oxidative damage in pathologic conditions (V Jaquet et al, Small-Molecule NOX Inhibitors: ROS-Generating NADPH Oxidases as Therapeutic Targets, Antioxidants & Redox. Signaling, 11(10): 2535-2552, 2009—Review). In following, it has been established that keratinocytes and fibroblasts generate ROS in response to UV light (S M Beak et al, Biochimie, 86: 425-429, 2004). These ROS responses can be blocked by NADPH oxidase inhibitors, raising the possibility that ROS generation even in response to ultraviolet light is not simply a physicochemical process, but involve NOX enzymes. Furthermore, it has been established that NOXderived ROS are involved in the regulation of expression and/or activation of matrix metalloproteases (K Bedard & K H Krause, Physiol and Pathophysiol, Physiol Rev 87: 245-313, 2007). While NOX2 occurs in normal cells, both NOX2 and NOX4 are expressed in melanoma cells. On the basis of antisense experiments, NOX4 has been suggested to promote cell growth in melanoma cells (S S Brar et al, Am J Physiol Cell Physiol, 282: c1212-c1224, 2002). Hence, blocking the undesirable actions of NOX enzymes may be a therapeutic strategy for treating oxidative stress-related pathologies, especially those arising from photo-damage.

Additional Factors

Certainly, UV radiation has a marked adverse effect on a number of biomolecular processes in the skin; however, among other factors and influences, air pollution also has a marked adverse effect (P Puri et al., Effects of air pollution on the skin: A review, *Indian J Dermatol Venereol Leprol.* 2017 83(4):415-423, 2017). Additionally, it is to be appreciated that such skin damage is not limited to the aforementioned biomolecular processes. For example, ultraviolet (UV) light enhances synthesis of matrix metalloproteases (MMPs) in human skin in vivo, and MMP mediated collagen destruction occurs in photo-aging. UV light and air pollutants also induce oxidative stress and pro-inflammatory mediators, such as transcription factors and chemokines, causing inflammation-induced skin damage. Hence, strategies to counter the effects of skin aging due to UV and air pollution exposure must be multifaceted and multidirectional if they are to be effective. Accordingly, efforts to slow down the aging process must endeavor to (1) achieve or establish antioxidant protection to limit direct oxidative damage to the cells, proteins, and DNA, (2) reduce the activity of oxidase enzymes, (3) control or mitigate inflammation and inflammatory responses to minimize inflammation-induced aging, (4) prevent degradation of extracellular matrix proteins by inhibiting matrix metalloproteases (MMPs) and (5) prevent photon- and enzyme-induced skin damage, among others.

Skin Structures

From the foregoing, it is evident that UV radiation has a marked detrimental effect on a molecular level in skin cells, from damage to DNA to the formation of ROS, and that the avenues of damage are numerous and far reaching. Furthermore, damage from exposure to UV radiation is not limited to the molecular level, but affects a host of other structures and processes that adversely affect the skin. However, these adverse effects are not limited to UV radiation exposure. Indeed, chronological aging and diseases, directly and indirectly, have a marked adverse effect on a broad number of biological processes in the skin as well as on the integrity of a number of skin structures and their efficacy and/or operation or function.

Perhaps the key underlying physiological change in aging skin is a thinning and general degradation of the skin, most notably a degradation and/or loss of various cells and/or chemical constituents necessary for maintaining the physiological characteristics of youthful skin. Specifically, as the skin naturally ages, the division rate of skin cells slows down causing an overall reduction in the number of cells and blood vessels that supply nutrients and other necessary building blocks for the skin which results in a significant decrease in the thickness of the epidermis. Concurrently, as the skin ages proteins, especially collagen and elastin fibers in the underlying layers of skin which provide the scaffolding for the surface layers, begin to weaken and deteriorate and/or manifest a deterioration in their cross-linking capabilities causing the skin to lose elasticity as well as resulting in a flattening of and concurrent loss of mechanical properties, including strength and flexibility, particularly, but not exclusively, in the dermal-epidermal junction (Neerken S, Lucassen G W, Bischop M A, Lenderink E, Nuijs T A, J Biomed Opt, 2004 March-April: 9(2)274-81 and Oikarinen, "The Aging of Skin; Chronoaging Versus Photoaging," Photodermatol. Photoimmunol. Photomed., vol. 7, pp. 3-4. 1990, both of which are incorporated by reference herein in their entirety).

The dermal-epidermal junction (DEJ) is a critical component of the skin and is composed of a network of structural proteins that provide a firm connection between the basal keratinocytes of the epidermis and the dermis. This structural network is made up of (1) the hemidesmosome-anchoring filament complex; (2) the basement membrane comprising two layers, the lamina lucida and the lamin dense, and (3) anchoring fibrils. The lamina lucida is a thinner layer and lies directly beneath the epidermal layer of basal keratinocytes. The thicker lamina dense is in direct contact with the underlying dermis. The basal keratinocytes are connected to the basement membrane via the hemidesmosome-anchoring complex and the basement membrane, in turn, is connected to the dermis via the anchoring fibrils. Each of these components of the DEJ has specific constituents, most notably laminins, integrins tenascin, and above all collagens, specifically collagen IV, and a very precise role to play (Allen J., Br. J. Dermatol. 1997 December; 137 (6): 907-15), (M. Aumailley, Kidney Internat., Vol 47, Suppl. 49 (1995), pp S-4-S-7). Concurrently, these structures are the target of immunologic injury in bullous pemphigoid and epidermolysis bullosa.

Collagen fibers are major elements of the dermis and collagens and the most abundant protein in the human body; the dermis alone is composed of approximately 75% collagen proteins in dry weight. So far, twenty-eight collagen species have been identified. Of these it has been reported that skin contains collagen types 1, 3, 4-7, 13, and 14, with the major collagen in the dermis being collagen type 1. Collagens that associate with the collagen type 1 fiber are classified as FACIT collagens and can provide additional mechanical properties to tissues. Collagens are characterized by repeated glycine-X-Y sequences and form triple-helical structures that are extensively modified after their secretion into the extracellular space. In immature tissues, such as those found in wound healing and fibrosis, collagen type 3 is expressed; however, it is not yet strong enough to support mature connective tissues. As the wound matures, collagen type 1 becomes dominant. Heterotypic type 1 and type 3 collagen fibrils are present in the dermis. Collagen type 4 individually forms a unique filament called a microfilament (T Nemoto et al., Viscoelastic Properties of the Human Dermis and Other Connective Tissues and Its Relevance to Tissue Aging and Aging-Related Disease, Intech, Chapter 7, DOI: 10.5772/50146 and refs cited therein), Elastic fiber comprises elastin and microfibrils. Since the dermis has be stretched to adapt to the movement of body parts, elasticity is a critical property of the dermis. Elastin, a unique molecule that stretches and shrinks, is secreted as tropoelastin (the soluble precursor of mature elastin) and is subsequently processed and cross-linked within the extracellular space. Cross-linking by lysyl oxidase and desmosine formation is a crucial step for the stabilization of elastin within tissues. Another element in elastic fibers is fibrillin-microfibril. Microfibrils are fibrous elements that are 10 nm in width and are comprised mainly of fibrillins. Fibrillin is a large glycoprotein that is rich in cysteine residues and homotypically assembles into a microfibril in a well-regulated manner. Fibrillins align in a parallel manner, from head to tail, in a staggered fashion within extracellular microfibrils. Other extracellular matrix (ECM) molecules, including microfibril-associated glycoproteins (MAGPs), latent TGF-beta binding proteins (LTBPs), collagen type 16, emilin, and versican, can associate with microfibrils through their binding affinity with fibrillins. Fibulins are yet another elastic fiber component, which can bridge elastin and microfibrils by their binding properties.

The dermis changes prominently with age; for example, the thickness of the dermis becomes thin and wrinkles appear. Biochemical collagen content and histological density of collagen fiber is reduced. Versican is a key molecule for viscoelasticity of the dermis (T Nemoto et al., Viscoelastic Properties of the Human Dermis and Other Connective Tissues and Its Relevance to Tissue Aging and Aging-Related Disease, Intech, Chapter 7, DOI: 10.5772/50146; & references cited therein). Loss or reduction of versican leads to impaired viscoelasticity of the dermis. Versican is heavily accumulated within solar elastosis, which is a hallmark of photo-aged skin and where elastic fiber components, including elastin and fibrillin-1, have accumulated (E F Bernstein et al., Differential Expression of the Versican and Decorin Genes in Photoaged and Sun-Protected Skin. Comparison by Immunohistochemical and Northern Analyses, Lab Invest, 72662669, 1995). Clinically, photo-aged skin is not viscoelastic and shows deep wrinkles Fibulins are a family of calcium-binding extracellular glycoproteins associated with basement membranes and elastic fibers in vertebrates. The fibulins do not form large homotypic aggregates, in contrast to many other ECM proteins, but they have the ability to join other supramolecular structures as diverse as basement-membrane networks, elastic fibers, several types of microfibrils and proteoglycans aggregates. Fibulin-1 is a prominent component of skin which is essential for the morphology of endothelial cells lining capillary walls and the integrity of small blood vessels [W S Argraves et al., Fibulins: physiological and disease perspectives. EMBO Rep, 4:1127-1131, 2003; R Timpl et al., Fibulins: A versatile family of extracellular matrix proteins, Mol Cell Biol, 4:479-489, 2003 in Viscoelasticity—From Theory to Biological Applications, book edited by Juan de Vicente, ISBN 978-953-51-0841-2, Published: Nov. 7, 2012].

Numerous efforts have been undertaken for improving the dermal-epidermal junction resulting in a number of successful, at least to some extent, techniques. For example, Marionnet et. al. have shown the utility of vitamin C in improving the DEJ formation in an in vitro human reconstructed skin model leading to a DEJ structure closer to that of normal young looking human skin (Marionnet C, Vioux-Chagnoleau C. Pierrard C, Sok J, Asselineau O, Bernard F. Meeting abstracts, 34.sup.th Annual European Society for dermatological Research Meeting, September 2004, Vienna, Austria). Similarly, Fisher et. al. have shown an improvement in the DEJ formation and extracellular matrix proteins arising from retinoids (Fischer G J and Voorhees J, J. Molecular mechanisms of retinoid actions in skin. FASEB J. 10, 1002-1013 (1998).

Certainly, while much effort has been directed to the DEJ, the DEJ is certainly not the only area of focus. Indeed, a number of investigators have shown the beneficial impact of topical application of retinoids on skin appearance as well as on various histological parameters such as a thickening of the epidermis including the stratum granulosum, an increase in the height of epidermal ridges or rates of the DEJ and the number of dermal papillae, a gradual displacement of age-related deposition of dermal elastin by collagen and peptidoaminoglycans, normalization of melanocyte function and an increase in the number of dermal fibroblasts. See, for example, Kligman, U.S. Pat. Nos. 4,603,146 and 4,877,805; Zelickson, A. S., J. Cutaneous Aging Cosmet. Dermatol., 1:4147 (1988); Weiss, J. S., JAMA, 259:527-532 (1988); J. Bhawan, Arch. Dermatol., 127:666-672 (1991); and Kligman, L. H., Connect. Tissue Res., 12:139-150 (1984). Similarly, Varani et. al. have shown vitamin A as antagonizing decreased cell growth and elevated collagen-degrading matrix metalloproteases while concurrently stimulating collagen accumulation in naturally aged human skin, Varani J, et. al., J Investigative Dermatology, 114:480-486, 2000). Dyer et. al. (U.S. Pat. No. 7,351,745) teach a method of applying a physiologically effective amount of an active agent, wherein said active agent is S-Methyl-L-Cysteine and S-Phenyl-L-Cysteine in a dermatologically pharmaceutically or physiologically acceptable vehicle, sufficient to increase expression levels of at least one gene selected from the group consisting of: Beta-catenin, Collagen 4. Collagen 7, Frizzled 10, Estrogen Receptor alpha, Hyaluronic acid synthase, and combinations thereof and for improving the condition and appearance of skin. Bernerd (US Patent Application: 2004/0005342) teaches the use of ascorbic acid or an analogue thereof in a pharmaceutically or cosmetically acceptable medium to increase the synthesis of tenascin and/or collagen VII for reinforcing the cohesion at the DEJ. Dal Farra et. al. (U.S. Pat. No. 7,211,269) teach a method for preparing cosmetic or dermatological compositions of a sufficient amount of peptides of sequence $(Gly-Pro-Gln)_n$-$NH_2$, wherein n is from 1 to 3, and wherein the amino acids can be in the form L, D or DL: these compositions being designed to promote adhesion between skin cells, to enhance cell adhesion, to provide curative and/or preventive treatment for aging skin symptoms (of physiological or solar origin) and to enhance skin appearance. In a preferred embodiment, the peptide is of sequence $(Gly-Pro-Gln)_2$-$NH_2$. Bonte et. al. (U.S. Pat. No. 6,641,848) teach the use of saponins or sapogenols, particularly those extracted from plants such as soya or Medicago, in cosmetology and for the manufacture of pharmaceutical compositions for treating the skin in order to increase the amount of collagen IV in the dermal-epidermal junction. Paufique (U.S. Pat. No. 6,531,132) describes a process for extracting an active principle from yeast whereby the active principle is used to retard the degradation of the dermal-epidermal junction to improve the surface condition of the skin. Dumas et. al. (U.S. Pat. No. 6,495,147) describe the use of D-xylose, esters thereof or oligosaccharides containing D-xylose for stimulating the synthesis and/or secretion of proteoglycans and/or glycosaminoglycans by the keratinocytes of a human in need thereof. Bonte et. al. (U.S. Pat. No. 6,471,972) teach a cosmetic treatment method for fighting against skin aging effects wherein the method comprises the application of at least one agent for promoting the adhesion of the keratinocytes of the epidermal basal layer to the dermal-epidermal junction, especially to the collagen IV of said junction, such as, in particular, a divalent metal salt or complex, preferably magnesium aspartate or magnesium chloride, optionally in association with a stimulant of collagen IV synthesis and/or a stimulant of collagen synthesis. LeSquer et. al. (WO 2002/015869) described combinations of ursolic acid and/or oleanolic acid with a specific palmitoyl pentapeptide Lys-Thr-Thr-Lys-Ser as synergistically increasing/stimulating the neosynthesis of compounds of the DEJ including collagen IV.

Despite all the efforts that have been undertaken to formulate effective compositions for improving the dermal-epidermal junction, current products are not entirely effective, Vitamin C and some of its derivatives are not photochemically or hydrolytically stable. In certain environments, especially in the presence of iron and hydrogen peroxide, Vitamin C can act as a pro-oxidant. Retinoids are very effective, but they also suffer from stability problems. Additionally, retinoids can also cause skin irritation, sensitization and are teratogenic. Plant extracts, if not standardized against key actives, oftentimes are not effective, Peptides are effective, but not fully characterized as yet. For example, though not manifest in short term use, some minor peptide impurities may cause adverse effects over long-term use. Consequently, the user oftentimes finds themselves with no results or an undesired result, e.g., irritation, sensitization, burning sensation, erythema, etc. of the skin.

Alternative approaches to improving the condition or appearance of aging skin that have received increasing attention involve the modulation of extracellular matrix proteins and matrix degrading enzymes and transcription factors. Representative disclosures in this area include: Mancini A, Di Battista J A, "Transcriptional regulation of matrix metalloprotease gene expression in health and disease", Front Biosci, 11:423-446, 2006. S Reitamo, A Remitz, K Tamai, and J Uitto, "Interleukin-10 modulates type I collagen and matrix metalloprotease gene expression in cultured human skin fibroblasts", Cin Invest, 1994, 94(6): 2489-2492, 1994 von Marcschall Z, Riecken E O, Rosewicz S, "Induction of matrix metalloprotease-1 gene expression by retinoic acid in the human pancreatic tumor cell line Dan-G", Br J Cancer, 80(7):935-939, 1999. Bair E L, Massey C P, Tran N L, Borchers A H, Heimark R L, Cress A E, Bowden G T, "Integrin- and cadherin-mediated induction of the matrix metalloprotease matrilysin in co-cultures of malignant oral squamous cell carcinoma cells and dermal fibroblasts", Exp Cell Res, 270(2):259-267, 2001. Nagahara 5, Matsuda 1, "Cell-substrate and cell-cell interactions differently regulate cytoskeletal and extracellular matrix protein gene expression", J Biomed Mater Res, 32(4):677-86, 1996 Smits P. Poumay Y, Karperien M, Tylzanowski P, Wauters J, Huylebroeck D, Ponec M and Merregaert J. "Differentiation-Dependent Alternative Splicing and Expression of the Extracellular Matrix Protein 1 Gene in Human Keratinocytes", J Invest Dermatol, 114:718-724, 2000, Reunamen N, Westermarck J, Hakkinen L, Holmstrom, Elo I, Eriksson J E, Kahari V M, "Enhancement of fibroblast collagenase (matrix metalloproteinase-1) gene expression by ceramide is mediated by extracellular signal-regulated and stress-activated protein kinase pathways", J Biol Chem, 273(9):5137-45, 1998. McKay I A, Winyard P, Leigh I M, Bustin S A, "Nuclear transcription factors: potential targets for new modes of intervention in skin disease", Br J Dermatol, 131(5):591-597, 1994.

As evident from the foregoing discussion, skin aging is a complex biological process influenced by a combination of endogenous or intrinsic and exogenous or extrinsic factors. Because of the fact that skin health and beauty is considered one of the principal factors representing overall "well-being" and the perception of "health" in humans, the development of anti-aging strategies has long been and continues to be a key focus of research and development efforts in the health and beauty arena [R Ganceviciene et al., Skin anti-aging strategies, Dermatoendocrinol. 4(3): 308-319, 2012 and refs cited therein], Chronic photodamage of the skin manifests itself as extrinsic skin aging (photoaging) wherein DNA photodamage and UV-generated reactive oxygen species (ROS) are the initial molecular events that lead to most of the typical histological and clinical manifestations of chronic photodamage of the skin. Wrinkling and pigmentary changes are directly associated with premature photo-aging and are considered its most important cutaneous manifestations. To date research and development efforts have focused on two main groups of compounds for use as anti-aging agents: the antioxidants and the cell regulators. Antioxidants, such as vitamins, polyphenols and flavonoids, reduce collagen degradation by reducing the concentration of free radicals in the tissues. Cell regulators, such as retinols, peptides and growth factors (GF), have direct effects on collagen metabolism and influence collagen production, Unfortunately, these efforts have been limited, providing marginal results owing to specificity of their actions and the myriad of mechanisms and processes involved, as detailed above.

Accordingly, there is an urgent and huge unmet need for effective methods and compositions that can prevent skin damage and reverse photoaging and/or chronological aging on multiple fronts simultaneously, thereby preventing and/or mitigating and/or delaying its onset.

Specifically, there is a need to provide methods and compositions having significant and marked efficacy in minimizing and/or preventing, most especially in reversing, chronic UV and air pollutant-induced skin damage on the molecular, including DNA, level as well as through the reduction in other UV-induced related biomarkers.

SUMMARY OF THE INVENTION

Surprisingly, it has now been found that the application, especially topical application, of certain aryl alkanones provides a significant and marked effect in minimizing and/or preventing, most especially in reversing, the molecular, micro- and macro-manifestation of skin aging, especially skin aging due to chronic UV-induced photodamage and air pollutant oxidative damage. These aryl alkanones manifest properties of both the antioxidants and the cell regulators and have broad effect across a multitude of molecular biological processes as well as physiological processes in the skin. Specifically, it has now been found that select aryl alkanones are able to reduce and/or eliminate the concentration of radicals by direct quenching of photoexcited states, direct scavenging of radicals, and/or inhibiting oxidase enzymes, such as NADPH oxidase, and also act as cell regulators in increasing the synthesis of extracellular matrix and dermo-epidermal genes/proteins.

In accordance with the present teaching there is provided a method of treating skin to mitigate, prevent and/or reverse the manifestation of skin aging said method comprising applying to the skin one or more aryl alkanones corresponding to the general Structure 1

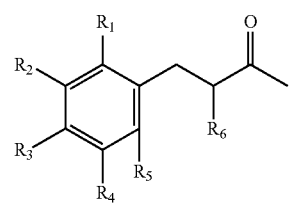

Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms. Most preferably, the aryl alkanone is applied topically in a carrier or as a component of a skin care and/or cosmetic composition.

In accordance with a second aspect of the present teaching there is provided topical compositions comprising a skin enhancing effective amount of one or more aryl alkanones corresponding to the general Structure 1

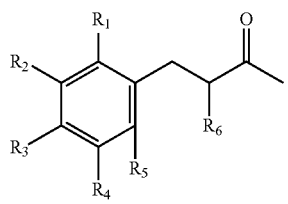

Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms, in a dermatologically acceptable carrier. Such topical compositions typically comprise from 0.01 to 20, preferably, from 0.1 to 10 weight percent of the aryl alkanone based on the total weight of the composition.

In accordance with a third aspect, of the present teaching there are provided improved cosmetic and skin care compositions, including therapeutic skin care compositions, wherein the improvement lies in the inclusion in such compositions of a skin enhancing effective amount, preferably from 0.01 to 20, more preferably from 0.1 to 10, weight percent, based on the total weight of the composition, of one or more aryl alkanones corresponding to the general Structure 1

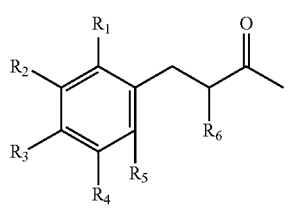

Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms. Exemplary cosmetic and skin care compositions include, make-up, foundation, eye shadow, lipstick, rouge, moisturizing compositions, sunscreen compositions, lip balm, rejuvenating creams, and the like.

DETAIL DESCRIPTION OF THE INVENTION

As used in the present specification, the following terms shall have the meanings as presented:

A "dermatologically acceptable vehicle" refers to a material that acts as a diluent, dispersant or carrier for the stated actives, especially the aryl alkanone(s), and is recognized in the industry as acceptable or suitable for use, preferably long term use, in skin contact and, to the extent appropriate or applicable, has been approved or is otherwise approvable by a regulatory agency of a government or governmental body or is listed in the U.S. Pharmacopoeia or other generally recognized pharmacopoeia for use on humans.

The term "improves" or "improved" is used to convey that the present invention changes either the characteristics and/or the physical attributes of the tissue to which it is being provided, applied or administered and/or influences the biomolecular activities and/or processes in the skin in a way that counteracts, directly or indirectly, the detrimental effects of UV exposure, air pollutant exposure, and/or skin aging.

The term "inhibiting" generally refers to the ability to prevent or delay the onset of a given event, process, action or reaction, or symptom or manifestation of a condition or disorder.

The term "optional" or "optionally" means that the subsequently described subject, event or circumstance may or may not occur, and that the description includes instances where the event occurs and instances where it does not and/or when the subject is present and when it is not present.

The terms "effective amount" and "skin enhancing effective amount" refer to the amount of the specified compound or composition that when applied to the skin is able to affect the desired effect whether on a molecular level, as evidenced by changes in the level or concentration of targeted materials, and/or on a macro level whereby visual or microscopic changes in the tissue are evident. Skin enhancing refers to both the ability to inhibit, prevent and/or preclude damage as well as the ability to reverse existing damage.

Erring on the side of caution and in an effort to avoid having overlooked or inadvertently omitted certain descriptive matter, particularly complementary and supplementary descriptive matter, it is hereby stated and affirmed that the technical publications as well as the patent and patent application publications mentioned herein are al incorporated herein in their entirety by this reference. Indeed, for example, while the current specification could present page after page of description of suitable dermatologically acceptable vehicles, supplemental or ancillary ingredients, and co-actives as well as various cosmetic and skin care compositions into which the aryl alkanones can be incorporated, such would not be productive as the same are well known and well recognized by those skilled in the art and those that come into being subsequent to the filing of this application will readily be appreciated as suitable as well In accordance with the present teaching here is provided a method of treating skin to mitigate, prevent and/or reverse the manifestation of skin aging said method comprising applying to the skin one or more aryl alkanones corresponding to the general Structure 1

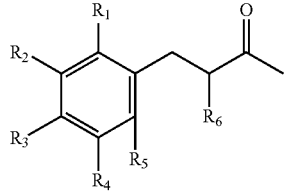

Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms. Most preferably, the aryl alkanone is applied topically in a carrier or as a component of a skin care and/or cosmetic composition.

In accordance with a second aspect of the present teaching there is provided topical compositions comprising a skin enhancing effective amount of one or more aryl alkanones corresponding to the general Structure 1

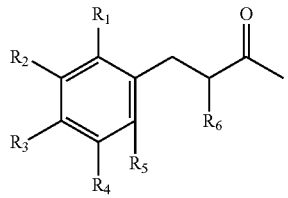

Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is=$COCH_3$ or $CO_2R_7$, wherein $R_7$ is a linear or branched alkyl having 1 to 8 carbon atoms, preferably from 1 to 6 carbon atoms, most preferably from 1 to 4 carbon atoms, in a dermatologically acceptable carrier. Such topical compositions typically comprise from 0.01 to 20, preferably, from 0.1 to 10 weight percent of the aryl alkanone based on the total weight of the composition, In accordance with a third aspect of the present teaching there are provided improved cosmetic and skin care compositions, including therapeutic skin care compositions, wherein the improvement lies in the inclusion in such compositions of a skin enhancing effective amount, preferably from 0.01 to 20, more preferably from 0.1 to 10, weight percent, based on the total weight of the composition, of one or more aryl alkanones corresponding to the general Structure 1

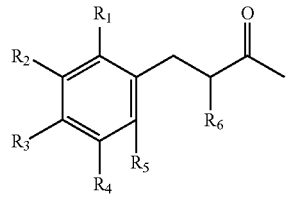

Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms. Exemplary cosmetic and skin care compositions include, make-up, foundation, rouge, moisturizing compositions, sunscreen compositions, lip balm, rejuvenating creams, and the like.

The key and critical aspect of the present teaching is the select aryl alkanones. As noted, aryl alkanones used in accordance with the present teaching correspond to Structure 1

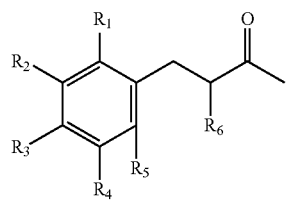

Structure 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 8 carbon atoms, preferably from 1 to 6 carbon atoms, most preferably from 1 to 4 carbon atoms; and $R_6$ is $COCH_3$ or $CO_2R_7$, wherein $R_7$ is a linear or branched alkyl having 1 to 8 carbon atoms, preferably from 1 to 6 carbon atoms, most preferably from 1 to 4 carbon atoms.

Preferred compounds according to Structure 1 are those wherein

Compound A. $R_1$, $R_2$, and $R_5$ are H and $R_4$ is an alkyl or alkoxy group of from 1 to 8, preferably from 1 to 6, more preferably from 1 to 4 carbon atoms, most preferably $OCH_3$, and $R_6$ is $COCH_3$ or $CO_2C_2H_5$;

Compound B. $R_1$ and $R_5$ are H, $R_2$ and $R_4$ are $OCH_3$, $R_3$ is OH, and $R_6$ is $COCH_3$ or $CO_2C_2H_5$;

Compound C. $R_1$, $R_2$, and $R_5$ are H, $R_4$ is $OCH_3$, $R_3$ is OH, and $R_6$ is $COCH_3$ or $CO_2C_2H_5$; and Compound D. $R_1$, $R_2$, and $R_5$ are H, $R_4$ and $R_3$ are alkoxy, which may be the same or a different alkoxy, and $R_6$ is $COCH_3$ or $CO_2C_2H_5$.

The most preferred compounds are those compounds of Structure 2 as follows:

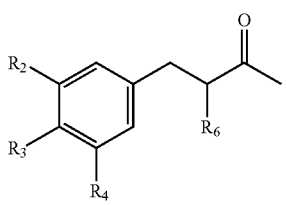

Structure 2

Exemplary preferred compounds include:

Compound 1 (Acetyl Zingerone): $R_2$ is H; $R_3$ is OH; $R_4$ is $OCH_3$; and $R_6$ is $COCH_3$;

Compound 2: $R_2$ is H; $R_3$ is OH; $R_4$ is $OCH_3$; and $R_6$ is $CO_2C_2H_5$;

Compound 3: $R_2$ and $R_4$ are H; $R_3$ is OH; and $R_6$ is $COCH_3$;

Compound 4: $R_2$ and $R_4$ are H; $R_3$ is OH; and $R_6$ is $CO_2C_2H_5$;

Compound 5: $R_2$ and $R_4$ are $OCH_3$; $R_3$ is OH; and $R_6$ is $COCH_3$;

Compound 6: $R_2$ and $R_4$ are $OCH_3$; $R_3$ is OH; and $R_6$ is $CO_2C_2H_5$;

Compound 7: $R_2$, $R_3$ and $R_4$ are $OCH_3$; and $R_6$ is $COCH_3$;

Compound 8: $R_2$, $R_3$ and $R_4$ are $OCH_3$; and $R_6$ is $CO_2C_2H_5$;

Compound 9: $R_2$ and $R_4$ are H; $R_3$ is $OCH_3$; and $R_6$ is $CO_2C_2H_5$; and Compound 10: $R_2$ and $R_4$ are H; $R_3$ is $OCH_3$; and $R_6$ is $COCH_3$.

Although the aryl alkanone could be applied to the skin directly, it is typically applied as a component of a composition. Most preferably, the composition comprises the aryl alkanone in a dermatologically acceptable carrier or excipient and/or as a component of a skin care and/or cosmetic composition and/or as a component of a topically applied pharmaceutical composition.

Generally speaking, the aryl alkanones may be combined with/incorporated into any known carrier or base composition employed in skin care/treatment compositions; especially those carriers and excipients that are suitable for long term and repeated application to the skin without manifesting sensitization or irritation or inflammation. Suitable carriers and excipients include any of the known topical excipients and like agents necessary for achieving the particular form of the skin care composition desired. Exemplary excipients include, e.g., mineral oils, silicone oils, and emulsifying agents as well as water, alcohol, or water/alcohol combinations, or other solvent(s) or solvent systems in which the aforementioned actives may be, e.g., soluble, dispersed, emulsified, etc. Preferably, though, the compositions according to the present teaching will include excipients and the like that create a substantially stable, homogenous composition and/or provide body, improved partition coefficient, and viscosity to the composition so that the aryl alkanone does not merely run off the skin once applied. Suitable carriers and carrier compositions are described at length in, for example, Gonzalez et. al.—U.S. Pat. No. 7,186,404; Aust et. al.—U.S. Pat. No. 7,175,834; Roseaver et. al.—U.S. Pat. No. 7,172,754; Simoulidis. et. al.—U.S. Pat. No. 7,175,835; Mongiat. et. al.—U.S. Pat. No. 7,101,536; Maniscalco—U.S. Pat. No. 7,078,022; Forestier et. al. U.S. Pat. Nos. 5,175,340, 5,567,418, 5,538,716, and U.S. Pat. No. 5,951,968; Deflandre. et. al.—U.S. Pat. No. 5,670,140; Chaudhuri—U.S. Pat. Nos. 6,831,191, 6,602,515, 7,166,273, 6,936,735, and U.S. Pat. No. 6,699,463; Chaudhuri et. al.—U.S. Pat. Nos. 6,165,450 and 7,150,876; Bonda et. al. U.S. Pat. No. 6,962,692; Rodan et. al.—U.S. Pat. No. 9,144,434, Wang et. al. U.S. Pat. No. 5,830,441 and Auspitz et. al.—US 2007/0110685 A1.

The final form of these compositions and their method of manufacture depend, in part, upon the mode of administration as well as the other ingredients to be incorporated into the composition. Accordingly, the compositions containing the aryl alkanones may be in form of solutions, suspensions, emulsions, capsules, capsules containing liquids, powders, creams, lotions, gels, sustained-release formulations, emulsions, aerosols, sprays, suspensions, and the like. In following, the compositions may be prepared by means of conventional mixing, dissolving, granulating, dragee-making, levigating, emulsifying, suspending, encapsulating, etc. All of such options and methods are conventional in the art.

The aryl alkanone is applied or administered in an effective amount. Most typically, as noted above, the aryl alkanone is applied or administered as a component of a composition comprising the aryl alkanone in a dermatologically acceptable carrier, alone or together with one or more co-constituents, which may be an active constituent which supplements the activity of the aryl'alkanone and/or provides another benefit to the skin and/or as part of a topical pharmaceutical composition such as those used the treatment for psoriasis, atopic dermatitis, and the like, and/or as part of a common topical composition such as a sunscreen composition, cosmetic composition, moisturizer, etc.

Where the aryl alkanone is part of a composition, it is typically present in said composition in an amount which, when the composition is applied in accordance with the instructions or common practice, is sufficient to achieve the desired effect. Typically, the amount of the aryl alkanone present in these compositions will be from 0.01 to 20, preferably from 0.1 to 10, weight percent based on the total weight of the composition.

As noted, the aryl alkanones are preferably incorporated into or combined with a carrier or other composition. Such compositions may have, as their primary objective, the application of the aryl alkanone or the aryl alkanone may be a supplemental or co-active ingredient. For example, the compositions optionally include an effective amount of one or more skin protective and/or treatment ingredients such as antioxidants, sunscreen actives, vitamins, anti-inflammatory agents, self-tanning agents, moisturizers, emollients, humectants, skin lighteners, anti-acne ingredients, compatible solutes and the like, and mixtures thereof, in their conventional amounts. Alternatively, or in addition thereto, these compositions may also include other ingredients that have no or little bearing upon the intended end-use or application of the treatment aspect of these compositions, but aid in the preparation and/or longevity thereof, such as solubilizers, surfactants, stabilizers, thickeners, preservatives, buffers, etc. and/or the aesthetic qualities thereof, e.g., dyes, perfumes, scents, opacifiers, colorants, etc. Furthermore, as previously mentioned, the aryl alkanone can be incorporated or added to existing skin care products, including cosmetics, general skin care products, and other pharmaceutical products.

It is impractical to attempt to list all of the ingredients which may be combined with the aryl alkanones and/or all the compositions into which the aryl alkanones may be incorporated. However, those skilled in the art will readily appreciate the same.

The amount of the aryl alkanone, especially the aryl alkanone composition, to be applied is generally that amount which is sufficient to provide a thin film of the composition to the treated skin. Typically, a small quantity of the composition, for example from 0.1 to 5 ml, is applied to the skin from a suitable container or applicator and spread over and/or rubbed into the skin using the hands or fingers or a suitable device. Preferably, the aryl alkanone composition is applied at least once daily until an improvement in skin appearance becomes apparent, typically, from 7 days to 6 months, depending on skin condition, the concentration of the active components used in the inventive method, the amount of composition used and the frequency with which it is applied. Most preferably, the aryl alkanone composition is applied continually, as a daily ritual, to constantly inhibit the effects of natural skin aging and, more importantly, the detrimental effects of sun exposure and air pollutants. In this regard, a user may adopt a routine of application of a aryl alkanone composition where the aryl alkanone is the key or a key active ingredient to address the already existing manifestation of skin aging and/or sun damage until resolved followed by the use of a daily moisturizer, sunscreen and/or cosmetic composition that also contains the aryl alkanone as a constant preventative and therapeutic treatment.

Having generally described the present method and compositions, attention is now drawn to the following examples and studies which demonstrate the surprising performance of the aryl alkanones in targeting and inhibiting the processes and sites most associated with skin aging and sun and air pollutant exposure damage. In the following examples, reference is made to the use of select compounds according to Structure 2 above.

EXAMPLES

Oxidative Stress and Skin

As noted in the Background above, UV light induces oxidative stress and pro-inflammatory transcription factors, cytokines, chemokines and enzymes causing inflammation-induced skin damage. Absent isolating oneself from UV light exposure, it becomes necessary to, among other factors, effect antioxidant protection so as to limit direct oxidative damage to the cells, proteins, and DNA. Using the method of W. Mullen et al. (Journal of Agricultural and Food Chemistry, 59(8):3754-3782, 2011) the antioxidant power of Compound 1 (acetyl zingerone above) and Compound 7 were compared to natural tocopherol, a well-known antioxidant, to assess their respective abilities to scavenge radicals and non-radical species.

TABLE 1

Antioxidant Power of Compound 1 vs Natural Tocopherol
(Antioxidant Power in μmole Trolox Equivalent/gram)

| Test | Compound 1 | Compound 7 | Tocopherol |
|---|---|---|---|
| Peroxyl radicals | 4,128 | Not determined | 813 |
| Hydroxyl radicals | 19,114 | Not determined | Not detected |
| Peroxynitrite | 1,139 | Not determined | 1 |
| Super oxide anion | Not Detected | Not determined | Not detected |
| Singlet oxygen | 7,180 | 6,359+ | 1,110 |
| Lipid peroxidation* | 0.48 | Not determined | 30 |

*$IC_{50}$ value in μg/ml; Squalene used as a substrate

The results are summarized in Table 1 which surprisingly shows that Compound 1 is a broad-spectrum scavenger of both radicals and non-radicals and far superior to the commonly used topical antioxidant Tocopherol. Additionally, the marked result shown for the antioxidant power of Compound 7, which does not have the free phenolic OH or double bond, in respect of singlet oxygen clearly demonstrates that the aryl alkanones work predominantly by a quenching mechanism rather than a scavenging mechanism as is the case for conventional antioxidants.

UV Exposure and Formation of Superoxide via NADPH Oxidase.

As also noted in the Background section above, there is strong evidence that nicotinamide adenine dinucleotide phosphate oxidase (NADPH), otherwise known as the NOX enzymes, are major contributors to oxidative damage in pathologic conditions (V Jaquet et al, Small-Molecule NOX Inhibitors: ROS-Generating NADPH Oxidases as Therapeutic Targets, Antioxidants & Redox Signaling, 11(10): 2535-2552, 2009—Review). Hence, it is believed that a mechanism for addressing UV damage is by blocking the undesirable actions of the NOX enzymes. In order to assess whether the aryl alkanones of the present teaching could serve to block NOX, a study of the NOX inhibitory activity of Compounds 1 and 8 were carried out by following the method described by A Valencia and I E Kochevar (Valencia & Kochevar, Nox1-Based NADPH Oxidase Is the Major Source of UVA-Induced Reactive Oxygen Species in Human Keratinocytes. J Invest Dermatol, 128:214, 2008), GKT 137831 (2-(2-chlorophenyl)-4-[3-(dimethylamino)phenyl]-5-methyl-1H-pyrazolo[4,3-c]pyridine-3,6(2H,5H)-dione) is a specific dual NADPH oxidase Nox1/Nox4 inhibitor (T Aoyama et al. Hepatology, 56(6):2316-2327, 2012) and was used as the positive control Results of these studies are summarized in the Table 2.

As shown in Table 2, both Compound 1 and Compound 8 were markedly effective in reducing NOS, activity induced by UVA as well as UVB radiation. The expanded testing with Compound 1 at two different levels demonstrated that the results were dose dependent with high statistical significance.

TABLE 2

Effect of Compounds 1 and 8 on the reduction of NOX activity

| | UV Type | | | | | |
|---|---|---|---|---|---|---|
| | UVB | | UVA | | | |
| | Keratinocytes* | | Keratinocytes** | | Fibroblasts | |
| | Amount used | | | | | |
| | 25 μg/ml | 50 μg/ml | 25 μg/ml | 50 μg/ml | 25 μg/ml | 50 μg/ml |
| Compound 1 | −11% | −29% | −27% | −38% | −27% | −33% |
| Compound 8 | | | | −17% | | −14% |

*dose dependency p ≤ 0.001
**dose dependency p ≤ 0.007

UV Exposure and Formation of Nitric Oxide Via Nitric Oxide Synthase

As noted above, large amounts of nitric oxide (NO) production following induction of the inducible NO synthase (iNOS) gene has been implicated in the pathogenesis of various inflammatory diseases. Additionally, it has also been established that NO produced in the skin by NO synthase combines with superoxide to form peroxynitrile, a highly reactive oxidant and mediator of tissue injury which is found to impair lipid peroxidation itself, oxidize lipid soluble antioxidants and cause DNA damage. Hence, agents that inhibit iNOS activity and, accordingly, NO production would be beneficial counteracting the adverse effects of UV exposure.

Accordingly, an investigation was undertaken to assess the efficacy of compounds according to the present teaching as compared to compounds that are closely structurally related thereto in inhibiting NO product. Specifically, Compound 1 was compared to Zingerone which has the structure

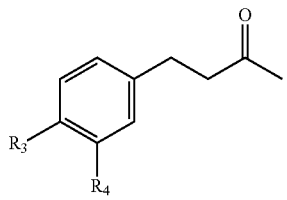

wherein $R_3$ is OH and $R_4$ is $OCH_3$. The results are presented in Table 3 where it is seen that Compound 1 is 2.5 times more effective in reducing iNOS activity than Zingerone.

TABLE 3

Reduction of iNOS activity

| Compounds | Compound 1 | zingerone |
|---|---|---|
| Amount used in µM ($IC_{50}$) values) | 194 | 364 |

UV Exposure & Formation of CPDs:

As noted above, among the various types of UV radiation induced DNA damage the most prominent is the formation of dipyrimidine lesions, most especially the cyclobutane pyrimidine dimers (CPDs) which are known to play a major role in skin cancer mutation.

Given the significance of CPDs in skin aging and damage, a study was undertaken to determine whether compounds of the present invention have the ability to directly protect the genome of skin cells from the mutagenic effect of UV light as evidenced by CPDs inhibition. The study was conducted in accordance with the method described by Mitchell et. al. [Mitchell, D L, The relative cytotoxicity of (6-4) photoproducts and cyclobutane dimers in mammalian cells. Photochem Photobiol, 48(1):51-57, 1988)] pursuant to which UVA- and UVB-induced formation of immediate CPDs (iCPDs) were determined. The results of this investigation are summarized in Table 4.

A second study was carried out, similar to the first, except that this time the analysis was in assessing the efficacy, if any, of the presently taught aryl alkanones in reducing UVA-induced delayed formation of CPDs (dCPDs). The results of this study are summarized in Table 5.

TABLE 4

% Reduction in the formation of iCPDs vs. Control

| | UVA/% Reduction in iCPDs | | UVB/% Reduction iCPDs | |
|---|---|---|---|---|
| *Compound # | Keratinocytes | Fibroblasts | Keratinocytes | Fibroblasts |
| Compound 1 | 73% | 45% | 44% | Not done |
| Compound 2 | 26% | Not done | 25% | 44% |
| Compound 8 | 42%+ | Not done | No done | No done |
| Zingerone | No effect | No effect | No effect | No effect |

*Concentration used: 25 µg/ml;
+Concentration used: 50 µg/ml

TABLE 5

% Reduction in the formation of dCPDs vs. control

| *Compound # | UVA/% Reduction in dCPDs | | | Comments |
|---|---|---|---|---|
| | Keratinocyte | Fibroblasts[1] | Melanocytes[2] | |
| Compound 1 | +0 hr.: ↓14%<br>1 hr.: ↓43%<br>2 hr.: ~0 | +0 hr.: ↓45%<br>1 hr.: ↓20%<br>2 hr.: ↓18% | 1 hr.: ↓70%<br>2 hr.: ↓25%<br>4 hr.: ~0 | No interference with the DNA repair process |
| Compound 2 | +0 hr.: ↓26%<br>1 hr.: ↓13%<br>2 hr.: ~0 | Not done | Not done | No interference with the DNA repair process |
| Compound 8 | Not done | +0 hr.: No effect<br>1 hr.: ↓35%<br>2 hr.: ↓52%<br>4 hr.: ↓32% | Not done | No reduction in the formation of dCPDs; Significant enhancement in DNA repair process seen after 1 hr. |
| Zingerone | No effect | No effect | Not done | No reduction in the formation of dCPDs |

*Concentration used 25 µg/ml
+Reduction in iCPDs
[1]Product incubated for 24 hrs. plus UVA irradiation; No delayed CPDs formation
[2]UVA irradiation first then product added; No irradiation after product addition QPES and Photooxidative Stress A study was undertaken to determine whether the aryl alkanones of the present invention have the ability to reduce photooxidative stress by physical Quencher of Photo-excited States (QPES) mechanism under UV light employing the method of Wondarak et al, (J Invest Dermatol, 119:489, 2002). Briefly, 100 ng (experiment 1) or 200 ng (experiment 2) of φX-174 RF bacteriophage supercoiled DNA was irradiated in the presence of 25 mg of filtered glycated bovine serum albumin (20 mg/ml BSA reacted for 3 weeks with 180 mg/ml glucose at 37° C.) in a final volume of 100 µl. The irradiation was performed in a 96 well plate without lid, with UVA lamp (Ultra-lum UVA-28T at 6.4 $mW/cm^2$) for 2 h, delivering a total energy of 46 J. Following irradiation 10 µl of the reaction mixture was mixed with 2 µl of loading buffer, resolved in 1% agarose gel (at 90V for 20 min) and stained with ethidium bromide (0.5 ng/ml). The intact (supercoiled) lower (faster-migrating) band and the UVA-damaged (uncoiled) higher (slower-migrating) band were visualized using Hoefer transilluminator. Photographs of the gels were then processed using NIH ImageJ and ratio of unwound (damaged) to supercoiled (intact) bands was calculated and used to assess the protective activity of test materials. The results are presented in Table 6.

As seen in Table 6 both Compound 1 and Compound 7 significantly reduced DNA damage. Furthermore, the results confirm a QPES mechanism of action, not an antioxidant mechanism, since Compound 7 does not have phenolic OH.

TABLE 6

% Reduction in UVA/AGE-albumin-induced DNA strand breaks

| Test Material (amount used) | % DNA strand breaks | % DNA strand protection |
|---|---|---|
| Irradiated control | 100 | 0 |
| Compound 1 (0.1 µg/ml) | 15 | 85 |

TABLE 6-continued

% Reduction in UVA/AGE-albumin-induced DNA strand breaks

| Test Material (amount used) | % DNA strand breaks | % DNA strand protection |
|---|---|---|
| Compound 1 (0.03 µg/ml) | 33 | 67 |
| Compound 1 (0.01 µg/ml) | 53 | 47 |
| Compound 1 (0.003 µg/ml) | 67 | 33 |
| Compound 7 (0.1 µg/ml) | 15 | 85 |
| Compound 7 (0.03 µg/ml) | 33 | 67 |

Separately, a study of the singlet oxygen quenching ability of Compound 1 and Compound 7 were evaluated. The results are presented in Table 7.

As seen in Table 7, both Compound 1 and Compound 7 demonstrated significant, comparable quenching ability with good statistical certainty (±10% error). Again these results confirm that the aryl alkanones, especially, Compound 1 and Compound 7 (which does not contain free phenolic OH or non-aromatic double bonds) are working as quenchers of singlet oxygen and not as scavengers as is the case for antioxidants.

TABLE 7

Singlet oxygen quenching

| Test Material | Singlet oxygen quenching (µMole Trolox Equivalent/g) |
|---|---|
| Compound 1 | 7,180 |
| Compound 7 | 6,359 |

UV Exposure and Mitochondrial Damage:

Again as noted in the Background, mitochondrial DNA (mtDNA) is susceptible to endogenous and environmental damage but lacks the full cohort of nuclear DNA repair mechanisms thereby threatening mitochondrial activity. Disruption of the mitochondrial polymerase by mtDNA damage is believed to underline skin damage and, consequently, many human diseases. Accordingly, a study was conducted to ascertain whether the compounds of the present invention have the ability to directly protect mitochondria and mitochondrial cell walls.

The study was conducted in accordance with the protocols of Berridge et al, (M V Berridge & A S Tan, Characterization of the cellular reduction of 3-(4,5-dimethylthiazol-2-yl)-2,5-diphenyltetrazolium bromide (MTT): subcellular localization, substrate dependence, and involvement of mitochondrial electron transport in MTT reduction, Arch. Biochem. Biophys. 303:474-482, 1993) and Voigt (W Voigt, Sulforhodamine B assay and chemosensitivity, Methods Mol Med, 110:39-48, 2005). Cellular metabolism is determined using the MTT assay to measure the activity of mitochondrial dehydrogenases, such as succinate dehydrogenase, which are implicated in the respiratory electron transport chain in mitochondria [M V Berridge & Tan Biochem Biophys, 303:474-482, 1993]. Additionally, the samples were subject to the Mitochondrial ToxGlo Assay (Promega Technical Manual, G8000 and G8001), which is a cell-based assay method that has been developed to quantify potential mitochondrial dysfunction as a result of xenobiotic exposure, using a sequential-addition, multiplexed chemistry. The results of these studies are summarized in Tables 8-10.

Table 8 presents the result on the effect of UVA radiation on cell metabolism 3 hours after irradiation. As indicated, Compound 1 improves cell metabolism, even at a very low use concentration. Table 9 presents the effect of 24 hour pre-incubation on UVA-induced mitochondrial damage measured by ATP production in human dermal fibroblasts. These results demonstrate that Compound 1 almost completely reversed ATP-damage, again, even at a very low use concentration. Finally. Table 10 presents the effect of 24 hour pre-incubation on UVA-induced plasma membrane disruption in human dermal fibroblasts. As indicated, Compound 1 almost completely reversed plasma membrane disruption, again at a very low use concentration. These studies demonstrate that the aryl alkanones have a marked and significant effect in preventing and/or reversing UV radiation induced mtDNA damage.

TABLE 8

Effect of UVA irradiation on cellular metabolism

| Compound | MTT (% Control) | p-value | Cell # (% Control) | p-value | Cell Metabolism Standardized to cell # (% Control) |
|---|---|---|---|---|---|
| Non-irradiated control | 100 | 1.000 | 100 | 1.000 | 100 |
| Irradiated control | 83 | 0.090 | 104 | 0.152 | 80 |
| Compound 1 (0.5 µg/ml) | 122 | 0.455 | 99 | 0.729 | 123 |
| Compound 1 (2 µg/ml) | 137 | 0.020 | 101 | 0.693 | 136 |
| Compound 1 (5 µg/ml) | 164 | 0.025 | 95 | 0.093 | 174 |

TABLE 9

24 h pre-incubation on UVA-induced mitochondrial damage

| Experimental conditions | ATP-related chemoluminescence (% Control) | p-value vs. non-irradiated control | Comments |
|---|---|---|---|
| Non-irradiated control | 100 | 1.000 | Target |
| UVA-irradiated control | 52 | 0.021 | 48% damage |
| Compound 1 (6.25 ug/ml) | 94 | 0.707 | Only 6% damage |
| Compound 1 (12.5 ug/ml) | 87 | 0.527 | Only 13% damage |

TABLE 10

UVA-induced plasma membrane disruption in human dermal fibroblasts

| Experimental conditions (24 hour Pre-incubation) | Plasma membrane disruption-related fluorescence (% Control) | p-value vs. non-irradiated control |
|---|---|---|
| Non-irradiated control | 100 | 0.000 |
| UVA-irradiated control | 166 | 1.000 |
| Compound 1 amount | | |
| 6.25 ug/ml | 125 | 0.019 |
| 12.5 ug/ml | 130 | 0.046 |
| 25 ug/ml | 117 | 0.009 |

*Statistically significant and dose-dependent reduction

Extracellular Matrix & Dermo-epidermal Genes/Proteins

As noted in the Background, while UV exposure is a major factor in skin damage and premature skin aging, skin aging is a natural progression most often arising from or correlating to adverse changes in or growing inefficiency of certain gene expressions which, in turn, have a marked adverse effect on a number of skin processes and structures. This is particularly so with respect to the extracellular matrix and dermal-epidermal junctions. Indeed, these areas have been a key focus of many and long standing efforts to address skin aging, particularly through gene manipulation and control.

In light of the efficacy of the aryl alkanones ire addressing many of the molecular/biomolecular processes damaged by UV exposure, a study was undertaken to assess whether these compounds would also be effective in addressing symptoms associated with non-UV induced skin aging including chronological aging as well as disease conditions that likewise adversely affect skin processes. The studies conducted involves DNA microarray, PCR array, cell culture, enzyme inhibitory activity.

Surprisingly, as shown in Table 11, it has been found that the select aryl alkanones according to the present teaching have a marked, beneficial impact on gene expression related to a number of skin processes and functions, including the extracellular matrix and the dermal-epidermal junction. Indeed, the results were broad spectrum, beneficially affecting many gene/protein expressions, suggesting that these compounds may be a utopian additive in the fight against skin aging.

TABLE 11

| Gene Expression Profile of Compound 1 | | | | |
|---|---|---|---|---|
| Gene | Full Name | Key Functions | Microarray | PCR array |
| Collagen | | | | |
| COL1A1 | Collagen, type 1, alpha 1 | Collagen fibers are major elements of the dermis and collagens are the most abundant protein in the human body; the dermis alone is composed of approximately 75% collagen proteins in dry weight. Twenty-eight collagens have presently been identified, the major collagen in the dermis being collagen, type 1. [Fisher GJ, Varani J, Voorhees JJ. Looking older: Fibroblast Collapse and Therapeutic Implications. Arch Dermatol, 144(5):666-672, 2008] | +1.6 | — |
| COL3A1 | Collagen, type 3, alpha 1 | | +1.7 | — |
| COL4A1 | Collagen, type 4, alpha 1 | | +1.6 | — |
| COL5A1 | Collagen, type 5, alpha 1 | | +4.1 | +2.7 |
| COL6A1 | Collagen, type 6, alpha 1 | | — | +1.5 |
| COL6A3 | Collagen, type 6, alpha 3 | | +1.8 | — |
| COL11A1 | Collagen, type 11, alpha 1 | | +1.6 | +1.9 |
| COL11A2 | Collagen, type 11, alpha 2 | | +5.2 | — |
| COL14A1 | Collagen, type 14, alpha 1 | | +4.3 | +2.1 |
| Elastin | | | | |
| ELN | Elastin | Elastin is a self-assembling, extracellular-matrix protein that is the major provider of tissue elasticity (Biochemistry and Cell Biology,88(2): 239-250, 2010) | +1.7 | ND |
| Fibulin | | | | |
| FBLN1 | Fibulin 1 | Calcium-binding extracellular glycoprotein associated with basement membranes and elastic fibers. Structural protein that contributes to the elastic properties of connective tissue fibers (J Histochem Cytochem, 43(4):401-411, 1995). | +1.9 | ND |
| Vimentin | | | | |
| VMN | Vimentin | Vimentin is required for cell motility, chemotactic migration, and wound healing. Vimentin modification is related to the loss of contractile capacity of fibroblasts caused by the structural breakdown of the intermediate filament system finally accelerating the process of aging | +1.7 | — |
| Tensin | | | | |
| TNS2 | Tensin 2 | Regulates cell motility and proliferation, FASEB J. 19(8):971-973, | +1.7 | ND |
| Versican | | | | |
| VCAN | Versican | Versican is a key molecule for viscoelasticity of the dermis (T Nemoto et al., Intech, Chapter 7, DOI: 10.5772/50146; & references cited therein). Loss or reduction of versican leads to impaired viscoelasticity of the dermis. | +1.7 | ND |

TABLE 11-continued

Gene Expression Profile of Compound 1

| Gene | Full Name | Key Functions | Microarray | PCR array |
|---|---|---|---|---|
| Fibromodulin | | | | |
| FMOD | Fibromodulin | Fibromodulin participates in the assembly of the collagen fibers of the extracellular matrix. FMOD knock-out (Fmod−/−) mice have very fragile skin [Adv Wound Care, 4(3):152-73, 2015] | +1.6 | ND |
| Laminin | | | | |
| LAMA4 | Laminin, alpha 4 | Laminins are a major component of the basal lamina (one of the layers of the basement membrane), a protein network, foundation for most cells and organs. The laminins are an important and biologically active part of the basal lamina, influencing cell differentiation, migration, and adhesion (Timpl R, et al. J Biol Chem, 254(19): 9933-9937, 1979) | +1.7 | — |
| LAMC1 | Laminin, gama 1 | | — | +2.0 |
| Integrin | | | | |
| ITGA1 | Integrin, alpha 1 | Integrin and ECM expression not only provide epidermal stem cell markers, but also regulate stem cell fate. Integrins do regulate epidermal stem cells in vivo (FN Watt et al., Cold Spring Harb Perspect Biol doi: 10.1101/cshperspect.a005124) | — | +2.2 |
| ITGA2 | Integrin, alpha 2 | | — | +1.6 |
| ITGA4 | Integrin, alpha 4 | | +1.6 | — |
| ITGB3 | Integrin, beta 3 | | — | +2.0 |
| ITGB5 | Integrin, beta 5 | | — | +1.7 |
| Tissue Inhibitory Metalloprotease (TIMP) | | | | |
| TIMP2 | | TIMPs are key regulators of the metalloproteases that degrade the extracellular matrix and shed cell surface molecules (K Brew et al., Biochim Biophys Acta, 1803(1): 55-71, 2010). TIMPs are also important regulators of ECM turnover, tissue remodeling and cellular behavior. | +1.5 | ND |
| TIMP3 | | | +5.1 | +2.4 |
| TIMP4 | | | +1.6 | ND |
| Matrix Metalloprotease | | | | |
| MMP3 | | The major proteases involved in ECM catabolism are the matrix metalloproteases (MMPs). MMP3 gene encodes an enzyme which degrades fibronectin, laminin, collagens III, IV, IX, and X, and cartilage proteoglycans (https://www.ncb.nim.nih.gov/gene/4314). | −2.4 | −2.5 |
| DNA Repair Genes | | | | |
| POT1 | protection of telomeres 1 | POT1 protects the ends of eukaryotic chromosomes from being recognized as DNA damage and from genetic instability (Mol Cell Biol, 28: 5251-5264, 2008) | +2.9 | — |
| MSH6 | mutS homolog 6 | Key mismatch repair protein involved in repairing DNA replication errors (Mol Cell Biol, 23:7992-8007, 2003) | +2.1 | — |

Collagens 1, 3 and 4 Boosting Property of Compound 1

Following on the foregoing, a study was performed focusing on collagens and the ability of the present aryl alkanones to manipulate collagen production and integrity. In this respect, it is to be recalled that skin aging is predominantly characterized by a reduction in the amount of Collagen type 1, especially in the rate of its production, and an increase in its degradation and glycation leading to a fragmentation of the collagen fibers. Collagen type 1 stimulation is considered an important activity for the mechanical integrity of skin tissue.

In this study, an investigation was performed in relation to the ability, if any, of the aryl alkanones to boost the production of Collagens 1, 3 and 4 proteins. The study was conducted using human fibroblasts in accordance with the method of J Dobak et at (J Dobak, J Grzybowski, F T Liu, B Landon, M Dobke, 1, 25-Dihydroxyvitamin D3 increases collagen production in dermal fibroblasts, J Dermatol Sci 1994; 8:18-24, 1994). In this study, the cells used were human dermal fibroblasts (HDF), passage 12 (Cell Applications, San Diego, Calif.) which underwent an incubation time of 6 days.

The results presented in Table 12 demonstrate a statistically significant stimulation of Collagen types 1, 3 and 4 by Compound 1 without a concurrent stimulation in metabolic activity and cell proliferation. Specifically, Compound 1 appears to stimulate the output of Collagen type 1, 3 and 4, especially when standardized to the overall cellular metabolism and cell numbers, but failed to stimulate general metabolism and proliferation of fibroblasts at the tested concentration range. MAP is used as the positive control: MAP being effective to cause cell proliferation at the levels tested.

TABLE 12

Collagen boosting effect of Compound 1

| Test Material | % Collagen 1 Bosting | p-value | % Collagen 3 boosting | p-value | % Collagen 4 Boosting | p-value |
|---|---|---|---|---|---|---|
| Compound 1 100 µg/ml | 173 | 0.000 | 146 | 0.000 | 245 | 0.000 |
| Compound 1 50 µg/ml | 118 | 0.135 | 111 | 0.203 | 145 | 0.000 |
| MAP 100 µg/ml | 209 | 0.000 | Not determined | — | 285 | 0.000 |
| MAP 50 µg/ml | 185 | 0.000 | Not determined | — | 214 | 0.000 |

MMP-1, MMP-3 and MMP-1 (Elastase) Inhibition

It is well established that MMPs are responsible for degrading key matrix proteins, for example, MMP-1 enzyme degrades collagens I, II, III, VII, VIII, X and gelatin; MMP-3 enzyme degrades fibronectin, laminin, collagens III, IV, IX, and X, and cartilage proteoglycans and MMP-12 enzyme degrades elastin, fibronectin, Collagen IV. Accordingly, the MMPs have been another target of study for gene manipulation as finding inhibitors of elastase enzymes would be useful in preventing the loss of skin elasticity and thus proliferation of skin sagging with age.

Another study was conducted in which the elastin and MMP activity of Compound 1 was evaluated. The methodology for the study of MMP-1 and MMP-3 activity was as follows:

A 0.1 g sample of Compound 1 was dissolved in 1 ml DMSO, then it was diluted 100× with Tris buffer (50 mM Iris pH 7.5, 150 mM NaCl, 2 mM $CaCl_2$, 5µ $ZnO_4$, 0.01% Brij-35) to make a stock solution. For the analysis, different concentrations of Compound 1 were used to determine the $IC_{50}$. The sample and 100 ng/ml MMP-1 enzyme (Anaspec) or MMP-3 enzyme (Anaspec) were incubated at 37° C. for 10 minutes before the addition of 2.25 µM PEPDAB008 substrate (Biozyme). The fluorescence signal was monitored at excitation of 485 nm and emission of 530 nm.

The methodology for the study of MMP-12 activity was as follows:

A 0.1 g sample of Compound 1 was dissolved in 1 ml DMSO, then it was diluted 100× with 1.4% randomly methylated cyclodextrin in Iris buffer (50 mM Tris pH 7.5, 150 mM NaCl, 2 mM $CaCl_2$, 5µ $ZnSO_4$, 0.01% Brij-35) to make a stock solution. For the analysis, different concentrations of Compound 1 were used to determine the $IC_{50}$. In the well: 0.2 mM substrate, 0.25 µg/ml enzyme, and sample were mixed and read according to the reference (TSA Thring et al. BMC Complementary and Alternate Medicine, 9, 27, 2009; https://doi.org/10.1186/1472-6882-9-27)

The results are presented in Table 13. As shown, the aryl alkanone, Compound 1, produced a significant inhibition of MMP-1, MMP-3 and MMP-12—again, demonstrating the surprising and broad spectrum anti-aging, skin rejuvenating and beneficial activity of Compound 1. Although not shown in Table 13, the study also found that Compound 1 upregulates the elastin gene: thus, not just inhibiting destruction but enhancing the integrity of the skin.

TABLE 13

MMP-1, MMP-3 and MMP-12 (Elastase) Inhibition

| Product | Type of MMP | Inhibitory concentration ($IC_{50}$) |
|---|---|---|
| Compound 1 | MMP-1 | 4.19 mM |
| Compound 1 | MMP-3 | 2.14 mM |
| Compound 1 | MMP-12 | 1.06 mM |

Clinical Validation of Skin Protection—Erythema

Erythema is the most obvious clinical sign of UV radiation exposure and becomes readily apparent within 6 hours or less of UV exposure and is maximal at about 24 hours [L L Hruza and A P Pentland, Mechanisms of UV-induced inflammation, J Invest Dermatol 1993:100(1):35S-41S]. COX dependent prostaglandin E2 (PGE2) is believed to be one of the mediators of UVR-induced erythema. Phospholipase A2 (PLA2), whose synthesis occurs only when skin is exposed to UV doses sufficient to cause erythema, is considered a rate limiting step in the generation of leukotrienes and prostaglandins, Hence, the two are intertwined in regards to erythema and their impact thereon. As noted in the Background, nitric oxide (NO) has now been established as a contributor to the UV erythema response. In light of the foregoing results, especially with respect to the iNOS activity, a clinical study was conducted to assess the skin protection property of Compound 1 against erythema. Formation of CPDs has also been implicated to cause erythema.

For the purpose of this study three sunscreen-free topical compositions were prepared, one with a low (0.5 wt %) and one with a high (2.0 wt %) level of Compound 1 and a control without Compound 1. The formulations of the two topical compositions containing Compound 1 are presented in Table 14: the control merely employed slightly more water in place of Compound 1. The test composition was prepared by combining the ingredients of Phase A1 and then dispersing the ingredients of Phase A2 one by one in Phase A1 while stirring and heating to 75° C. The ingredients of Phase B were combined and heated to 75° C. after which Phase B is added to Phase A with good mixing. The mixture is then homogenized at moderate speed for 3-5 min. The mixture is then cooled to 40° C. with propeller agitation until mixture is fully homogeneous. Thereafter, Phase C is added to the mixture with continued mixing.

TABLE 14

Formulation of Clinical Study Protective Lotion

| INCI name | Trade Name/Supplier | Formulation (% w/w) A | B |
|---|---|---|---|
| Phase A1 | | | |
| Water | Water(demineralized) | 80.5 | 82.0 |
| Disodium EDTA | Versene Na/Dow | 0.10 | 0.10 |
| Glycerine | Emery 916/BASF | 2.00 | 2.00 |
| Butylene Glycol | Butylene Glycol/Ruger | 1.50 | 1.50 |
| Phase A2 | | | |
| Xanthan Gum | Keltrol ® CG-T/CP Kelko | 0.20 | 0.20 |
| Phase B | | | |
| C12-15 Alkyl Benzoate | Finsolv TN/Innospec | 5.00 | 5.00 |
| Acetyl Zingerone (Compound 1) | Synoxyl ® AZ/Sytheon | 2.00 | 0.50 |
| Phenethyl Benzoate | X-Tend 226/Ashland | 2.00 | 2.00 |
| Glyceryl Stearate, PEG-100 Stearate | Arlacel 165/Croda | 2.00 | 2.00 |
| Shea Butter | Shebu Refined/Rita | 1.50 | 1.50 |
| Dimethicone | Dimethicone 200/100cst | 1.00 | 1.00 |
| Cetyl Alcohol | Crodacol C-70/Croda | 1.00 | 1.00 |
| Ammonium Acryloyldimethyltaurate VP Copolymer | Aristoflex AVC/Clariant | 0.60 | 0.60 |
| Phase C | | | |
| Benzyl Alcohol, Ethylhexylglycerine, Tocopherol | Euxyl 900K/Shulke | 0.60 | 0.60 |
| Total | | 100.00 | 100.00 |

Notes: pH - 5.5-6.0;
Viscosity - 40,000-60,000 mPas (Brookfield RVT, Spindle C, 10 rpm) at 25° C.

Fourteen human volunteers participated in this study in which a thin coat of each of the formulations was applied twice a day for seven days to separate areas of the volunteer's back. The treated areas were then exposed to UV light to induce erythema (low and high dose). 2xMED (Minimal erythemal dose) was applied after 7-day product application. Low dose meaning barely visible skin redness and high dose meaning clearly visible skin redness achieved by applying 25% higher UV exposure than low dose. In order to quantify the effect, the average L-, a- and ITA (Individual Typology Angle) values were determined for each of the test sites prior to irradiation/UV exposure ("Pre-Irr") and following irradiation/UV exposure ("Post-Irr").

Table 15 presents the results attained in this clinical study. As evident from the results, it is clear that Compound 1, even at low concentrations, demonstrated a marked reduction in the manifestation of erythema, as evidenced by the significant difference in the delta or change in the a* and ITA° values in those areas that were treated with the Compound 1 containing lotions as compared to the control areas.

TABLE 15

% Reduction in a* value and ITA°

| Formulation | % reduction in a* value | | % reduction in ITA° | |
|---|---|---|---|---|
| | low MED | high MED | low MED | high MED |
| A | 43.5 | 29.2 | 14.3 | 35.7 |
| B | 33.3 | 38.5 | 11.1 | 14.3 |

Practical Consumer Formulations

As described, the aryl alkanones can be formulated into carriers for application of the aryl alkanone or into other topical compositions and products for periodic, especially everyday use. Table 16 presents the formulation of a broad spectrum clear sunscreen spray composition having an SPF of at least 50. This sunscreen composition is prepared by preparing a pre-mix of Phase B and heating that to 75° C. with stirring until the mixture is completely free of solids. Concurrently, pre-mixes of the ingredients of Phase A and Phase C are prepared. Thereafter, Phase A and Phase C are added to Phase B at 50° C. with continued mixing.

TABLE 16

Broad Spectrum Clear Sunscreen Spray

| INCI name | Trade Name/Supplier | % w/w |
|---|---|---|
| Phase A | | |
| Ethanol | Ethanol | 40.00 |
| VA/Butyl Maleate/Isobornyl Acrylate Copolymer | Advantage Plus/Ashland | 2.00 |
| Phase B | | |
| Avobenzone | Eusolex 9020/EMD | 3.00 |
| Trimethoxybenzylidene Pentanedione* | Synoxyl ® HSS/Sytheon | 2.50 |
| Homosalate | Eusolex HMS/EMD | 10.00 |
| Octisalate | Eusolex OS/EMD | 5.00 |
| Diisopropyl Adipate | Dermol DIA/Alzo | 10.00 |
| Phase C | | |
| Phenethyl Benzoate | X-tend 226/Ashland | 20.00 |
| C12-15 Alkyl Benzoate | Finsolv TN/Innospec | 5.00 |
| Isosorbide Dicaprylate | HydraSynol ™ DOI/Sytheon | 2.00 |
| Acetyl Zingerone (Compound 1) | Synoxyl ® AZ/Sytheon | 0.50 |
| Total | | 100.00 | in-vivo SPF 56 (FDA protocol; 5 subjects); Critical wavelength: 376 nm

Table 17 presents the formulation of a hydrating broad spectrum sunscreen oil composition having an SPF of at least 30. This hydrating sunscreen composition is prepared by preparing a pre-mix of Phase B and heating that to 75° C. with stirring until the mixture is completely free of solids. Concurrently, pre-mixes of the ingredients of Phase A and Phase C are prepared. Thereafter, Phase A and Phase C are added to Phase B until a uniform mixture is attained.

TABLE 17

Hydrating Broad Spectrum Sunscreen Oil

| INCI name | Trade Name/Supplier | % w/w |
|---|---|---|
| Phase A | | |
| Octyldodecanol | Jarcoll-20CG/Jarchem | 27.80 |
| Disobutyl Adipate | Dermaol DIBA/Alzo | 10.00 |
| Dicapryl Ether | Cetiol OE/BASF | 18.00 |
| Isomayl Laurate | Dermofeel Sensolve/Dr Stramans | 10.00 |
| Isosorbide dicaprylate | HydraSynol DOI/Sytheon | 4.00 |
| Dipropylene Glycol Dibenzoate | Finsolye PG-22/Innospec | 2.00 |
| Phenethyl Benzoate | X-tend226/Ashland | 5.00 |
| Tocopheryl Acetate | Vitamin E Acetate/BASF | 0.20 |
| Silicon Polyester 1 | Cosmosurf DGSi/Ultra Chemical | 2.00 |
| Acetyl Zingerone (Compound 1) or Compound 8 | Synoxyl ® AZ/Sytheon | 0.50 |

TABLE 17-continued

Hydrating Broad Spectrum Sunscreen Oil

| INCl name | Trade Name/Supplier | % w/w |
|---|---|---|
| Phase B | | |
| Avobenzone | Eusolex 9020/EMD | 3.00 |
| Trimethoxybenzylidene Pentanedione | Synoxyl ® HSS/Sytheon | 2.50 |
| Homosalate | Eusolex HMS/EMD | 10.00 |
| Octisalate | Eusolex OS/EMD | 5.00 |
| Total | | 100.00 |

In-vivo SPF 32 (FDA protocol; 5 subjects); Critical wavelength 375 nm

Table 18 presents the formulation of a broad spectrum sunscreen lotion composition having an SPF of at least 45. This sunscreen composition is prepared by combining the ingredients of Phase A1; then dispersing Phase A2 in A1 while stirring and heating the mixture to 75° C. Separately, the ingredients of Phase B are combined and heat to 75° C. Phase B is then added to combined Phase A1/A2 with good mixing. The mixture is then homogenized at moderate speed for 3-5 min while adding Phase C (adjust pH to 5.5-6.0). Cool batch to 40° C. with propeller agitation until mixture is homogeneous. This mixture is then added to Phase D with continued mixing.

TABLE 18

Broad Spectrum Sunscreen Lotion*

| INCl name | Trade Name/Supplier | % w/w |
|---|---|---|
| Phase A | | |
| Water | Water(demineralized) | 53.90 |
| Disodium EDTA | Versene Na/Dow | 0.10 |
| Butylene Glycol | Butylene Glycol/Ruger | 2.00 |
| Glycerine | Emery 916/BASF | 2.00 |
| Propyl Gallate | Propyl Gallate/Sigma-Aldrich | 0.10 |
| Phase A2 | | |
| Xanthan Gum | Keltrol ® CG-T/CP Kelko | 0.15 |
| Phase B | | |
| C12-15 Alkyl Benzoate | Finsolv TN/Innospec | 5.00 |
| Tribehenin PEG-20 Esters | Emulim 22/Gattefosse | 2.00 |
| Glyceryl Stearate, PEG-100 Stearate | Arlacel 165/Croda | 1.50 |
| Octocrylene | Eusolex OCR/EMD Chemicals | 10.00 |
| Homosalate | Eusolex HMS/EMD Chemicals | 10.00 |
| Octyl Salicylate | Eusolex OS/EMD Chemicals | 5.00 |
| Avobenzone | Eusolex 9020/EMD Chemicals | 2.00 |
| Acetyl Zingerone (Compound 1) | Synoxyl ® AZ/Sytheon | 0.50 |
| Cetyl Alcohol | Crodacol C-70/Croda | 1.00 |
| C30+ Olefin/Undecylenic Acid Copolymer | Performa V 6112/New Phase Technologies | 1.00 |
| Dimethicone | Dow Corning 200,100 cst/Dow Corning | 1.00 |
| Ammonium Acryloyldimethyltaurate/VP Copolymer | Aristoflex AVC/Clariant | 0.50 |
| Phase C | | |
| Phenoxyethanol, Hexylene Glycol, Caprylyl Glycol | Lexgard HPO/Inolex | 1.00 |
| Phase D | | |
| Beta-Cyclodextrin | Cavamax W7/Wacker | 0.25 |
| Water | Water(demineralized) | 1.00 |
| Total | | 100.00 |

*In-vivo SPF 45; Critical wavelength 378 nm

Table 19 presents the formulation of an anti-aging for daily use. In addition to the presence of the aryl alkanone, Compound 1, this formulation also includes bakuchiol as a co-active/synergist in delaying and/or reversing the effects and manifestation of skin aging. This composition is prepared by combining the ingredients of Phase A1 and then dispersing therein the ingredients of Phase A2 one by one while stirring and heating to 75° C. Separately, the ingredients of Phase B are combined and heat to 75° C. after which Phase B is added to the combined Phase A1/A2 with good mixing. The mixture is then homogenized at moderate speed for 3-5 min while adding Phase C and, as necessary, adjusting the pH to 5.5-6.0. The mixture is then allowed to cool while adding Phase D. Once the mixture cools to 40° C., Phases E and F are added and the mixture mixed with propeller agitation until mixture is homogeneous.

TABLE 19

Age-Defying Day Cream

| INCl name | Trade Name/Supplier | % w/w |
|---|---|---|
| Phase A1 | | |
| Water | Water(demineralized) | 73.85 |
| Disodium EDTA | Versene Na/Dow | 0.10 |
| Glycerin | Emery 916/BASF | 2.00 |
| Butylene Glycol | Butylene Glycol/Ruger | 2.00 |
| D Panthenol | Panthenol/BASF | 0.50 |
| Phase A2 | | |
| Xanthan Gum | Keltrol ® CG-T/CP Kelko | 0.10 |
| Acrylates/C10-30 Alkyl Acrylate Crosspolymer | Carbopol Ultrez 21/Lubrizol | 0.30 |
| Sucrose Stearate | Sisterna SP50C /MMP | 1.50 |
| Phase B | | |
| Simmodsia Chinensis (Jojoba Oil) | Jojoba Oil/Jean Intl. | 3.00 |
| Shea Butter | Shebu Refined/Rita | 1.50 |
| Behenyl Alcohol | Lanette 22/BASF | 1.25 |
| Potassium Cetyl Phosphate | Amphisol ® K/DSM | 1.00 |
| Stearic Acid | Pristerene ® 4911/Croda | 1.00 |
| Dimethicone | Dow Corning 200,50 cst/Dow Corning | 5.00 |
| Natural Beeswax | Beeswax/Rita | 1.50 |
| Isosorbide Dicaprylate | HydraSynol ™ DOI/Sytheon | 2.00 |
| Acetyl Zingerone (Compound 1) or Compound 2 | Synoxyl ® AZ/Sytheon | 0.50 |
| Alpha Tocopherol | Vitamin E/BASF | 0.20 |
| Ammonium Acryloyldimethyltaurate/VP Copolymer | Aristoflex AVC/Clariant | 0.30 |
| Phase C | | |
| Sodium Hydroxide | Sodium Hydroxide (50% sol) | 0.20 |
| Phase D | | |
| Bakuchiol | Sytenol ® A/Sytheon | 1.00 |
| Phase E | | |
| Phenoxyethanol, Ethylhexyglycerine | Euxyl PE 9010/Schulke | 1.00 |
| Phase F | | |
| Fragrance | Women's FragranceK3258/ | 0.20 |
| Total | Carrubba | 100.00 |

Notes:
pH - 5.5-6.0 Viscosity - 80,000-100,000 mPas (Brookfield RVT, Spindle C, 10 rpm) at 25° C.

Table 20 presents a formulation for protecting skin against air pollution for daily use. In addition to the presence of the aryl alkanone, Compound 1, this formulation also includes barrier protectants, namely, Isosorbide dicaprylate and Isosorbide disunflower seedate as co-active/synergist in protecting skin against the onslaught of air pollutants. This composition is prepared by combining phase I and then dispersing phase A2 in phase A1 while stirring and heating phase A to 75° C. Phase B ingredients then combined and heated to 75° C. Phase B is added to phase A with good mixing. The mixture is then homogenized at high speed for 5 min. The batch is allowed to cool to 40° C. and then phase C and D are added slowly with gentle stirring until the mixture is homogeneous.

TABLE 20

Rich Barrier Protection Cream against Air Pollution

| INCI name | Trade Name/Supplier | |
|---|---|---|
| Phase A1 | | |
| Water (demineralized) | | 74.35 |
| Disodium EDTA | | 0.10 |
| Glycerin | Glycerin 99%/Ruger | 2.50 |
| Phase A2 | | |
| Sodium acrylates copolymer, Lecithin | Lecigel/Lucas Meyer | 0.90 |
| Phase B | | |
| Caprylic/Capric Triglycerides | Myritol 318/BASF | 4.00 |
| Steareth-10 | Brij S 10/Croda | 1.50 |
| Tocopheryl Acetate | Vitamin E Acetate/DSM | 0.10 |
| Stearyl/PPG-3 Myristyl Ether Dimer Dilinoleate | Liquiwax PolyIPL/Croda | 1.00 |
| Butyrospermum Parkii (Shea) Butter | Shea Butter Refined/Rita | 2.50 |
| Glyceryl Stearate | Cerasynt Q/Ashland | 2.50 |
| Cetyl Alcohol | Crodacol C-70/Croda | 1.75 |
| Dimethicone | DC, 200/100CST/Dow Corning | 1.00 |
| Isosorbide Dicaprylate | HydraSynol ™TM DOI/Sytheon | 2.00 |
| Isosorbide Disunflowerseedate | HydraSynol ™ IDL/Sytheon | 2.00 |
| Acetyl Zingerone (Compound 1) | Synoxyl ® AZ/Sytheon | 0.50 |
| Phase C | | |
| Phenoxyethanol, Ethylhexylglycerine | Euxyl PE 9010/Schulke | 0.85 |
| Citrus Reticulata (Tangerine) Peel Oil | Tangerine Oil/Beige | 0.25 |
| Citrus Bergamia (Bergamot) Peel Oil | Bergamot Oil/Premier | 0.10 |
| Phase D | Zemea/DuPont | 2.00 |
| Propanediol | | |
| Propyl Gallate | Propyl Gallate/Sigma-Aldrich | 0.10 |
| Total | | 100.00 |

Notes:
pH value: 5.5-6.0; Viscosity: 30,000-45,000 cps (Brookfield RVT, spindle C, Helipath) at 25° C.

Without further elaboration, it is believed that one skilled in the art, using the preceding description, can utilize the present invention to its fullest extent. Furthermore, while the present invention has been described with respect to aforementioned specific embodiments and examples, it should be appreciated that other embodiments, changes and modifications utilizing the concept of the present invention are possible, and within the skill of one in the art, without departing from the spirit and scope of the invention. The preceding preferred specific embodiments are, therefore, to be construed as merely illustrative, and not limitative of the remainder of the disclosure in any way whatsoever.

I claim:

1. A method for treating or reversing the manifestation of skin damage and premature skin aging due to UV-photo and oxidative damage and air pollutant oxidative damage comprising topical administration of an effective amount of one or more aryl alkanones having the structure

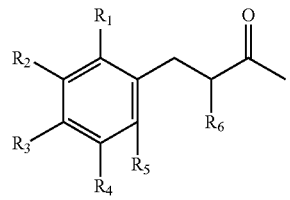

wherein $R_1$, $R_2$, $R_3$, $R_4$ and $R_5$ which may be the same or different, are independently H, OH, alkyl or alkoxy wherein the alkyl or alkoxy groups are linear or branched and have from 1 to 8 carbon atoms; and $R_6$ is $COCH_3$ or $CO_2R_7$ wherein $R_7$ is a linear or branched alkyl group having 1 to 8 carbon atoms.

2. The method of claim 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 6 carbon atoms.

3. The method of claim 1 wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 4 carbon atoms.

4. The method of claim 1 wherein the aryl alkanone has the formula

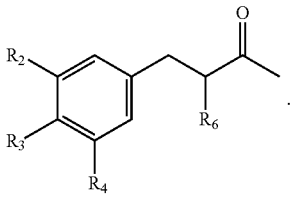

5. The method of claim 1 wherein the aryl alkanone is applied as part of a topical composition comprising a dermatologically acceptable carrier.

6. The method of claim 1 wherein the amount of aryl alkanone present in the composition is from 0.01 to 20 weight percent based on the weight of the composition.

7. The method of claim 5 wherein the amount of aryl alkanone present in the composition is from 0.1 to 10 weight percent based on the weight of the composition.

8. The method of claim 5 wherein the composition is a cosmetic composition selected from make-up, foundation, eye shadow, lipstick, and rouge.

9. The method of claim 5 wherein the composition is a skin care composition selected from moisturizing compositions, sunscreen compositions, lip balm, and skin rejuvenating creams.

10. The method of claim 5 wherein the composition is a skin care/protective composition applied topically on skin before, during and after sun exposure.

11. The method of claim 10 wherein the composition additionally contains one or more sunscreens, antioxidants, skin hydrators, barrier builders, anti-aging and/or skin lightening ingredients.

12. The method of claim 1 wherein the aryl alkanone is acetyl zingerone.

13. A method for treating or reversing the manifestation of skin damage and premature skin aging due to a degradation or disruption in or an interference with the production and/or integrity of the dermal-epidermal junction, the extracellular matrix, collagen and/or elastic fibers of the skin and their physiological processes comprising topical administration of an effective amount of one or more aryl alkanones having the structure

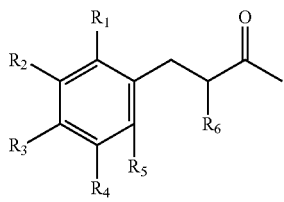

wherein $R_1$, $R_2$, $R_3$, $R_4$ and $R_5$ which may be the same or different, are independently H, OH, alkyl or alkoxy wherein the alkyl or alkoxy groups are linear or branched and have from 1 to 8 carbon atoms; and $R_6$ is $COCH_3$ or $CO_2R_7$ wherein $R_7$ is a linear or branched alkyl group having 1 to 8 carbon atoms.

14. The method of claim 13 wherein $R_1$, $R_2$, $R_3$, $R_4$ and $R_1$, which may be the same or different, are independently H, OH, alkyl or alkoxy wherein the alkyl or alkoxy groups are linear or branched and have from 1 to 6 carbon atoms.

15. The method of claim 13, wherein $R_1$, $R_2$, $R_3$, $R_4$ and $R_5$, which may be the same or different, are independently H, OH, alkyl or alkoxy wherein the alkyl or alkoxy groups are linear or branched and have from 1 to 4 carbon atoms.

16. The method of claim 13 wherein the aryl alkanone has the formula

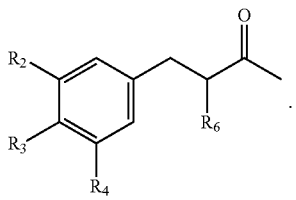

17. The method of claim 13 wherein the aryl alkanone is applied as part of a topical composition comprising a dermatologically acceptable carrier.

18. The method of claim 17 wherein the amount of aryl alkanone present in the composition is from 0.01 to 20 weight percent based on the weight of the composition.

19. The method of claim 17 wherein the amount of aryl alkanone present in the composition is from 0.1 to 10 weight percent based on the weight of the composition.

20. The method of claim 17 wherein the composition is a cosmetic composition selected from make-up, foundation, ee shadow, lipstick, and rouge.

21. The method of claim 17 wherein the composition is a skin care composition selected from moisturizing compositions, sunscreen compositions, lip balm, and skin rejuvenating creams.

22. The method of claim 17 wherein the composition is a skin care/protective composition applied topically on skin before, during and after sun exposure.

23. The method of claim 22 wherein the composition additionally contains one or more sunscreens, antioxidants, skin hydrators, barrier builders, anti-aging and/or skin lightening ingredients.

24. The method of claim 13 wherein the aryl alkanone is acetyl zingerone.

25. The method of claim 13 wherein the degradation or disruption in or the interference with the production and/or integrity of the dermal-epidermal junction, the extracellular matrix, collagen and/or elastic fibers and their physiological processes is a manifestation of a human disease.

* * * * *